(12) United States Patent
Johnson et al.

(10) Patent No.: US 7,972,271 B2
(45) Date of Patent: Jul. 5, 2011

(54) APPARATUS AND METHOD FOR PHASED SUBARRAY IMAGING

(75) Inventors: Jeremy Johnson, Santa Rosa, CA (US); Mustafa Karaman, Istanbul (TR); Butrus T. Khuri-Yakub, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1170 days.

(21) Appl. No.: 11/709,347

(22) Filed: Feb. 21, 2007

(65) Prior Publication Data
US 2007/0208254 A1 Sep. 6, 2007

Related U.S. Application Data

(63) Continuation-in-part of application No. 10/696,592, filed on Oct. 28, 2003, now abandoned.

(51) Int. Cl.
*A61B 8/14* (2006.01)
(52) U.S. Cl. .......................................................... 600/459
(58) Field of Classification Search ................... 600/459
See application file for complete search history.

(56) References Cited

U.S. PATENT DOCUMENTS

| | | | |
|---|---|---|---|
| 4,387,597 A | 6/1983 | Brandestini |
| 4,553,437 A | 11/1985 | Luthra et al. |
| 4,586,135 A | 4/1986 | Matsumoto |
| 4,839,652 A | 6/1989 | O'Donnell et al. |
| 5,269,307 A | 12/1993 | Fife et al. |
| 5,278,757 A | 1/1994 | Hoctor et al. |
| 5,461,389 A | 10/1995 | Dean |
| 5,465,722 A | 11/1995 | Fort et al. |
| 5,520,186 A | 5/1996 | Deitrich |
| 5,579,770 A | 12/1996 | Finger |
| 5,581,517 A | 12/1996 | Gee et al. |
| 5,617,862 A | 4/1997 | Cole et al. |
| 5,623,928 A | 4/1997 | Wright et al. |
| 5,667,373 A | 9/1997 | Wright et al. |
| 5,675,550 A | 10/1997 | Ekhaus |
| 5,676,147 A | 10/1997 | Petrofsky et al. |
| 5,784,336 A | 7/1998 | Gopinathan et al. |
| 5,793,701 A | 8/1998 | Wright et al. |
| 5,940,123 A | 8/1999 | Daigle et al. |

(Continued)

OTHER PUBLICATIONS

L.F. Nock et al., "Synthetic Receive Aperture Imaging with Phase Correction for Motion and for Tissue Inhomogeneities. I: Basic Principle," IEEE Trans. Ultrason., Ferroelect., Freq. Contr., vol. 39, pp. 489-495 (1992).

(Continued)

*Primary Examiner* — Long V Le
*Assistant Examiner* — Saurel J Selkin
(74) *Attorney, Agent, or Firm* — Lumen Patent Firm

(57) ABSTRACT

An invention for coherent array image formation and restoration is taught. The invention is applicable for both 2D and 3D imaging using either 1D or 2D arrays, respectively. A transducer array is subdivided into subarrays, each subarray having a number of adjacent array elements. All elements of each subarray transmit and receive in parallel. The signals received from each subarray are delayed and summed to form scan lines, or beams. The low-beam-rate beams formed from each subarray are upsampled and interpolated prior to forming high-beam-rate images. Depending on the subarray geometry, a subarray-dependent restoration filter is also applied to the subarray beams. The restored beams from each subarray are combined to form the final high-beam-rate image. The invention significantly reduces the front-end hardware complexity compared to conventional methods such as full phased array imaging with comparable image quality.

47 Claims, 13 Drawing Sheets

U.S. PATENT DOCUMENTS

| | | | |
|---|---|---|---|
| 5,951,479 | A | 9/1999 | Holm et al. |
| 5,980,458 | A | 11/1999 | Clark |
| 6,013,032 | A | 1/2000 | Savord et al. |
| 6,016,285 | A | 1/2000 | Wright et al. |
| 6,042,547 | A | 3/2000 | Wright et al. |
| 6,066,099 | A | 5/2000 | Thomenius et al. |
| 6,071,240 | A | 6/2000 | Hall et al. |
| 6,126,602 | A | 10/2000 | Savord |
| 6,201,900 | B1 | 3/2001 | Hossack et al. |
| 6,360,027 | B1 | 3/2002 | Hossack et al. |

OTHER PUBLICATIONS

M. Karaman, "Ultrasonic Array Imaging Based on Spatial Interpolation," 3rd IEEE International Conference on Image Processing, pp. 745-748 (1996).

Ö. Oralkan et al., "Capacitive Micromachined Ultrasonic Transducers: Next Generation Arrays for Acoustic Imaging?," IEEE Trans. Ultrason., Ferroelect., Freq. Contr., vol. 49, pp. 1596-1610 (2002).

J. A. Johnson et al., "Phased Subarray Processing for Underwater 3D Acoustic Imaging," presented at Oceans '02, MTS/IEEE (2002).

J. Johnson et al., "Synthetic Phased Array Image Formation and Restoration," ICASSP, IEEE International Conference on Acoustics, Speech and Signal Processing—Proceedings, vol. 3, pp. 2885-2888 (2002).

J. A. Johnson et al., "Image Formation and Restoration Using Multi-Element Synthetic Array Processing," Proceedings of SPIE The International Society for Optical Engineering, 2002.

J. A. Johnson et al., "Phased Subarray Imaging for Low-Cost, Wideband Coherent Array Imaging," Proceedings of the IEEE Ultrasonics Symposium (2003).

Jeremy A. Johnson et al., "Coherent Array Imaging Using Phased Subarrays—Part I: Basic Principles," (2003).

Jeremy A. Johnson et al., "Coherent Array Imaging Using Phased Subarrays—Part II: Simulations and Experimental Results," (2003).

APPARATUS AND METHOD FOR PHASED SUBARRAY IMAGING

CROSS REFERENCE TO RELATED APPLICATIONS

This application is a continuation in part of U.S. application Ser. No. 10/696,592, filed on Oct. 10, 2003 now abandoned, and entitled "Apparatus and Method for Phased Subarray Imaging".

FIELD OF THE INVENTION

The present invention relates generally to an apparatus and method for phased subarray imaging, including image reconstruction, in an ultrasound imaging system. More particularly, by acquiring low-beam-rate images with a series of subarrays, interpolation and spectral modification, the present invention allows high-beam-rate images to be obtained while reducing the complexity of the front-end electronics in the ultrasound imaging system.

BACKGROUND OF THE INVENTION

Real-time medical ultrasound imaging has played an increasingly important role in the diagnosis and treatment of disease. Ultrasound imaging is used for routine diagnostic procedures in obstetrics, gynecology, cardiology, and gastroenterology. The vast majority of ultrasound systems in use today provide two-dimensional (2D) cross-sections of the anatomy. While other imaging modalities such as magnetic resonance imaging and x-ray computed tomography have provided three-dimensional (3D) images since their inception, only recently have 3D ultrasound imaging systems become commercially available. These systems have the potential to revolutionize medical imaging by providing 3D visualization of the anatomy and blood flow in real-time.

Conventional hardware and methods used for 2D ultrasound systems do not scale well to achieve similar 3D imaging systems. Modern 2D ultrasound scanners use a long 1D-transducer array having roughly 128 elements. Transducer array length and number of elements used is chosen based on several design parameters, including operating frequency and desired lateral resolution. An equivalent 3D imaging system capable of achieving similar resolutions in both azimuth and elevation would require a square 2D transducer array with 128 elements per side, or a total of 16,384 elements. A first challenge one faces when implementing such a system is fabricating the transducer array with reasonable yields.

A second challenge caused by a large channel count for a 3D ultrasound system is implementing the highly parallel front-end electronics required. Front-end hardware has become one of the most space- and power-consuming parts of a typical ultrasound imaging system. This is especially true since the advent of digital beamforming to vary transmit and receive directions and focal lengths, which has greatly reduced back-end hardware requirements. Unfortunately, the analog nature of the front-end hardware has not experienced an equal reduction in cost and size. High-end commercial ultrasound machines still house the analog and mixed-signal, front-end electronics within a base unit, requiring costly and bulky probe cables that contain dedicated coaxial transmission lines for each transducer element.

Modern 2D imaging systems require this complex set of front-end electronics because they typically use conventional full phased array (FPA) imaging, which requires that all array elements be simultaneously active during transmit and receive. See, for example, A. Macovski, "Medical Imaging Systems" (Prentice Hall, Englewood Cliffs, N.J., 1983). As shown in FIG. 1, in an FPA imaging system 100, for every transducer element that is active for a given firing event (110, 112, 114, 116, 118, 120, 122, 124), an independent front-end transmit (126, 128, 130, 132, 134, 136, 138, 140) and receive (142, 144, 146, 148, 150, 152, 154, 156) electronics channel must perform pulse generation, transmit/receive switching, amplification, filtering, time-gain compensation and digital-to-analog conversion in parallel. These electronics are the primary contributor to the bulk, cost, and power consumption of a typical ultrasound imaging system. In addition to high front-end hardware complexity, the large number of received signals required to form each beam causes a significant increase in transmit beamformer 158 and receive beamformer 160 complexity. The implementation of precision delay lines for beam steering also places a large burden on the beamforming hardware. Using all elements for transmit and receive results in the best image quality, improves signal-to-noise ratio (SNR) by maximizing total transmitted signal power, improves overall sensitivity for receiving echo signals, and has a very high frame rate since only one transmission or firing is required for each transmit direction. While electronic components continue to become smaller, faster, and cheaper, it is still not feasible to implement a full set of channels required for a 2D transducer array for 3D ultrasonic imaging.

The need to reduce the number of channels in a 3D imaging system has been recognized for some time, and several approaches have been presented in the art. One approach is the use of sparse arrays, which define a fixed subset of active elements that span a full aperture of the array. Different methods for choosing active elements include random and periodic distributions. Other array geometries intended to reduce the channel count include boundary arrays and a Mill's cross array. While these methods successfully reduce the channel count of the system, they suffer from high side lobes (and thus poor contrast resolution) and low signal-to-noise ratio (SNR).

Alternative beamforming methods have also been suggested. As shown in FIG. 2, classical synthetic aperture (CSA) imaging techniques employing a single channel (or a few neighboring channels) for transmit and receive minimize the hardware complexity. In a CSA imaging system 200, a transmit/receive controller 210 provides drive signals to an active element 216 via front-end transmit electronics 212 and a multiplexer 214 and receives received signals via the multiplexer 214 and front-end receive electronics 218. See, for example, U.S. Pat. No. 4,839,652. CSA was first used with linear arrays with reconstruction in the spatial domain, but has since been modified for use with circular arrays and frequency-domain reconstruction methods have also been developed. For a standard linear array method, a single processing channel is time-multiplexed across all transducer elements. Since only a single element is used for both transmit and receive, the complexity of the front-end electronics is kept to an absolute minimum; however, transmitted power and receive sensitivity are minimal and lead to low SNR. Each image pixel is reconstructed using all echo scans; time separation between scans leads to tissue motion artifacts. When used to construct images from an array with an element pitch equal to half of a minimum wavelength, CSA also suffers from high grating lobes. To avoid the grating lobes, element pitch is typically chosen to be a quarter of the minimum wavelength, but at the expense of reducing the physical aperture (and the related lateral resolution) by a factor of two for the same element count. CSA also requires multiple transmissions for each transmit direction and adversely impacts the frame rate.

In synthetic phased array (SPA) imaging with a single active element per data acquisition step, each image pixel is formed by coherent summation of signal contributions from every transmit/receive element combination. (SPA imaging is also shown in FIG. 2.) See, for example, U.S. Pat. Nos. 4,586,135 and 5,465,722. SPA processing produces images with comparable resolution and SNR to the FPA images with lower front-end complexity. However, there is a significant increase in the number of transmissions for each image frame with the usual adverse impact on the frame rate. In addition, the technique is limited by a limited transmit/receive power from a single active channel, which necessitates especially low electronic noise front-end electronics.

Array imaging techniques have continued to strike compromises between CSA and FPA, aiming to improve the SNR of CSA methods and reducing the number of channels required for FPA imaging. An early proposal for reducing the number of active channels in phased array imaging systems did so by transmitting on a single central portion of the array and receiving on a number of overlapping or adjacent subarrays. See, for example, U.S. Pat. No. 4,553,437 and L. F. Nock et al., "Synthetic Receive Aperture Imaging with Phase Correction for Motion and for Tissue Inhomogeneities. I: Basic Principle," IEEE Trans. Ultrason., Ferroelect., Freq. Contr., vol. 39, pp. 489-95 (1992). Later developments improved the frame rate of subarray imaging by acquiring a subset of the beam lines and interpolating the others. See, for example, M. Karaman, "Ultrasonic Array Imaging Based on Spatial Interpolation," $3^{rd}$ IEEE International Conference on Image Processing, pp. 745-748 (1996) and U.S. Pat. No. 5,940,123. These methods, however, use 1D lateral interpolation filters and thus only produce successful results for relatively narrowband imaging. Recent proposals include transmitting from multiple elements to emulate a more powerful transmit element in SPA imaging, although a correction for motion and phase aberration would be required. A similar method proposes transmitting from five virtual elements and using the full aperture in receive in order to achieve the higher frame rates needed for 3D imaging with a 2D transducer array.

Real-time ultrasound imaging systems represent a tradeoff between front-end electronic complexity, image quality, SNR and frame rate. The proposals in the prior art do not successfully combine the advantages of CSA imaging in terms of reduced front-end complexity with the high quality image, high SNR and high frame rate associated with FPA imaging. Accordingly, there remains a need for a novel imaging system that combines the advantages of FPA and CSA imaging systems.

OBJECTS AND ADVANTAGES

In view of the above, it is a primary object of the present invention to provide an apparatus and method for phased subarray imaging, including image reconstruction, in an ultrasound imaging system. The phased subarray imaging of this invention provides a high-beam-rate image and allows a reduction in the front-end electronic complexity of the ultrasound imaging system.

These and numerous other objects and advantages of the present invention will become apparent upon reading the following description.

SUMMARY

The objects and advantages of the present invention are secured by an apparatus and method for phased subarray (PSA) imaging. An array of transducers is divided into a set of subarrays each having multiple adjacent elements. Energy is transmitted with a transmit focal length from a subarray and complex responses to this energy are received by the subarray. The active subarray is multiplexed across the full array of transducers. Each subarray is fired multiple times to acquire $Q_S$ beams, each defined by a direction in beam space and a plurality of receive focal lengths, that constitute a low-resolution subarray image with a low beam rate. The low-beam-rate subarray images are interpolated and spectrally modified to reconstruct high-beam-rate subarray images each having Q beams using at least one filter. The filter is varied for the subarrays. Appropriate weighting is applied to the high-beam-rate subarray images that are then combined to produce a high-beam-rate PSA image.

In an alternate embodiment, one subarray is used to transmit energy and another subarray is used to receive responses to this energy. The pair of transmit and receive subarrays are multiplexed across the full array of transducers.

In another embodiment, PSA imaging is performed for energy transmitted to a plurality of transmit focal lengths.

In another embodiment, the subarrays have a fixed number of adjacent elements. In another embodiment, the subarrays have a variable number of adjacent elements. In another embodiment, adjacent subarrays overlap one another and, therefore, have a number of common adjacent elements. In another embodiment, the overlap is fixed for all the subarrays. In another embodiment, the overlap between the subarrays is variable across the array. In yet another embodiment, there is no overlap between the subarrays, and different subarrays are used to transmit and receive energy.

The amount of overlap is chosen to ensure that an entire coarray (a measure of the spatial frequency content in the ultrasound imaging system) is covered by the subarrays and thus no image information is lost. There is a tradeoff between the number of subarrays, the amount of overlap and the frame rate. Reducing the number of subarrays and the amount of overlap results in a nonuniform coarray, which is not desirable for imaging. Therefore, in yet another embodiment, additional restoration filtering is applied to the high-beam-rate subarray images to restore the coarray for the PSA image to that of an FPA image.

In another embodiment, for sufficiently narrowband signals a filter for interpolation and spectral modification is a 1D or 2D filter for 2D or 3D imaging, respectively. In another embodiment, for wideband signals the filter for interpolation and spectral modification is a 2D filter or a 3D filter, for 2D or 3D imaging respectively.

In another embodiment, the subarrays have same number of said adjacent elements and the overlap of the subarrays is equal to half of the number of the adjacent elements in each of the subarrays and the filter for interpolation and spectral modification is a subarray-dependent bandpass filter with subarray-dependent gain or weighting.

In another embodiment, the filter for interpolation and spectral modification is varied for at least some of the subarrays as a function of the receive focal length.

In another embodiment, the upsampling and interpolation is varied for at least some of the subarrays.

In yet another embodiment, PSA imaging for at least some of the subarrays is repeated a plurality of times and the resulting high-beam-rate subarray images are averaged to improve the signal-to-noise ratio.

PSA imaging allows the number of front-end electronic channels to be reduced while maintaining high image quality as determined by a high-beam-rate and the signal-to-noise ratio. The quality of the final image is comparable to that achieved using FPA imaging for regions near the transmit focal length. The cost of PSA imaging is a reduction in the frame rate and SNR relative to FPA imaging. When the subarrays contain a fixed number of adjacent elements and neighboring subarrays overlap by less than half the number of adjacent elements in each subarray, the frame rate reduction is less than a factor of 2 for 2D imaging and less than a factor of 4 for 3D imaging.

BRIEF DESCRIPTION OF THE FIGURES

The objectives and advantages of the present invention will be understood by reading the following detailed description in conjunction with the drawings, in which.

DETAILED DESCRIPTION OF THE EMBODIMENTS

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

Figure 5:
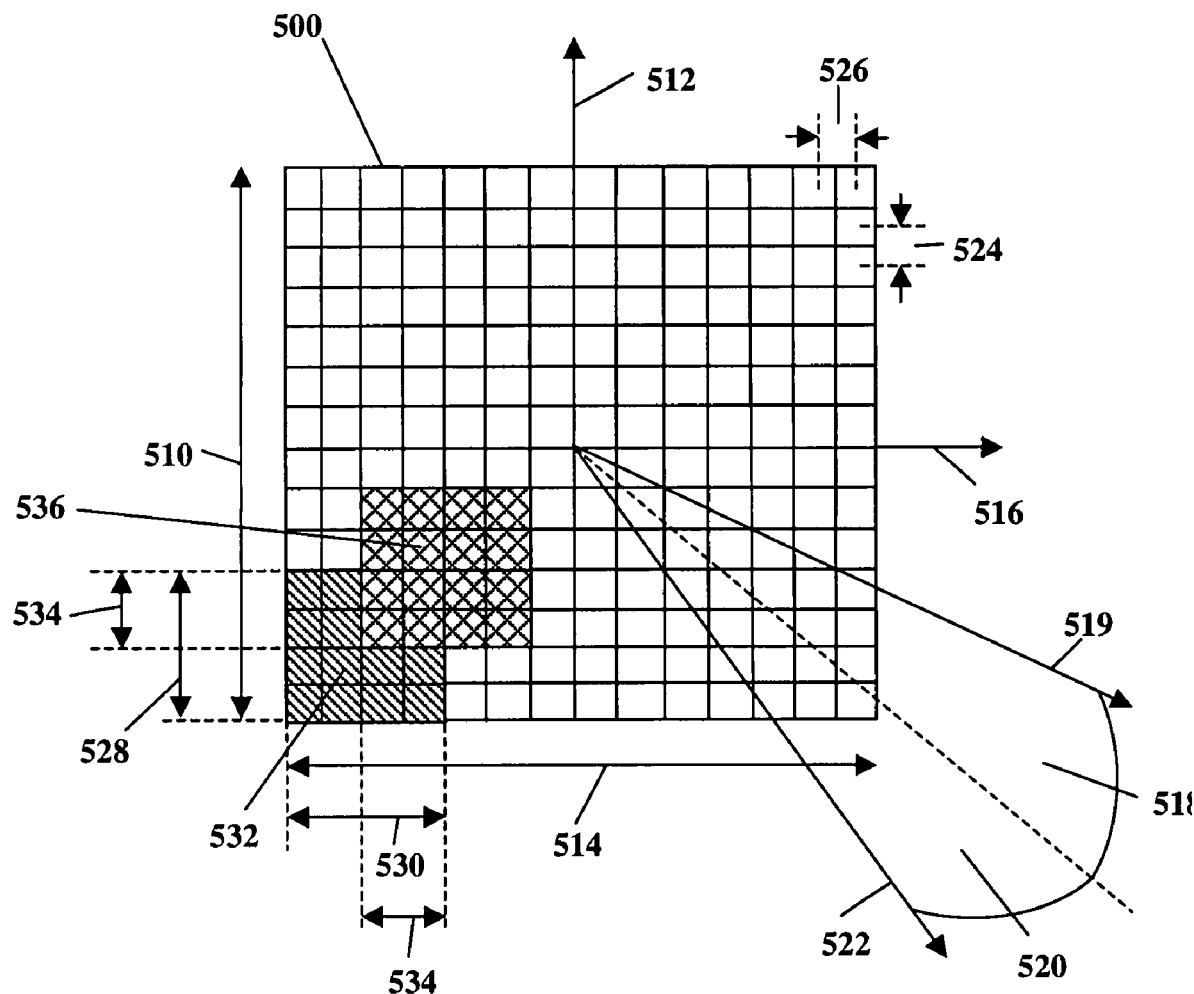
FIG. 5 is a diagram illustrating a 3D ultrasound imaging geometry including a 2D transducer array according to the present invention.

The basic geometry of a wideband pulse-echo sector-scanned 3D ultrasound imaging system is shown in FIG. 5. There is a 2D transducer array 500 having $N_1$ elements 510 along a first lateral direction 512 and $N_2$ elements 514 along a second lateral direction 516. Azimuth angle $\theta_1$ 518 and elevation angle $\theta_2$ 520 for radial direction 519 correspond to first lateral direction 512 and second lateral direction 516. Axial direction 522 is normal to the plane defined by the first lateral direction 512 and the second lateral direction 516.

The best resolution in the 3D ultrasound imaging system is obtained by minimizing the width of point spread function (PSF) in all three directions 512, 516 and 522. The width of the PSF in the first lateral direction 512 and the second lateral direction 516 is determined by the Fourier transform of an effective aperture function in these directions. Therefore, a wider effective aperture will lead to improved resolution along the corresponding lateral direction 512 and 516. The lateral PSF and thus the lateral resolution are also improved as the temporal frequency is increased or the spatial wavelength is decreased (the temporal frequency and the spatial wavelength being related by the speed of sound). Because the lateral PSF is a function of angle, the lateral resolution in Cartesian coordinates will improve with decreasing radius. Axial width of the PSF, which determines axial resolution, is solely determined by a pulse function in the wideband pulse-echo ultrasound imaging system. The axial resolution therefore improves with shorter pulse lengths. For a fixed modulation frequency, a shorter carrier signal results in an increase of the bandwidth.

For a rectangular transmit aperture and receive aperture, the effective aperture, given by the convolution of the transmit aperture and the receive aperture, is pyramidal and has a triangular cross-section. The corresponding lateral PSF has a sinc-squared response. The central lobe of the PSF is proportional to wavelength $\lambda$ divided by the effective aperture width D. The lateral spatial frequency response or coarray is determined by the inverse Fourier transform of the lateral PSF. The coarray is simply a scaled version of the effective aperture. Like the PSF, the coarray characterizes the resolution of the ultrasound imaging system, i.e., how sensitive the system is to image features of different spatial frequencies.

Ultrasound array imaging systems involve several sampling schemes. The effective aperture is a sampled version of a continuous effective aperture reflecting the discrete spacing $d_1$ 524 and spacing $d_2$ 526 between elements in the array 500. In the frequency domain, sampling results in a periodic repetition of the lateral PSF. In array imaging, the aliases are referred to as grating lobes and result in distortions of the image if they lie in the visible region. The visible region is defined as the range for azimuth angle $\theta_1$ 518 and elevation angle $\theta_2$ 520 during transmission and reception between $-\pi/2$ and $\pi/2$ or, for $s_1 = \sin\theta_1$ and $s_2 = \sin\theta_2$ between $-1$ and $1$. To avoid grating lobes in the visible region, the array 500 must be sampled with a period less than half of minimum wavelength ($\lambda_{min}$) in the pulse function. In addition, a finite number of beams or scan lines are determined over limited azimuth 518 and elevation 520 sector angles $\Theta_1$ and $\Theta_2$, with transmit and receive directions equally spaced in $s_1$ and $s_2$. For FPA, the minimum number of samples (beams) to avoid aliasing are given by the Nyquist beam sampling rates $$Q_1 \geq \frac{4N_1 d_1}{\lambda_{min}} \sin\left(\frac{\Theta_1}{2}\right)$$

and $$Q_2 \geq \frac{4N_2 d_2}{\lambda_{min}} \sin\left(\frac{\Theta_2}{2}\right).$$

The number of samples cannot be fractional, so $Q_1$ and $Q_2$ are typically chosen to be the smallest integers that satisfy these equations. For the wideband pulse-echo ultrasound imaging system, there is also sampling along the axial direction at a temporal sampling rate $f_{sample}$. As a consequence of the beam and temporal sampling, k-space representations of the resolution such as the PSF are periodic along the lateral spatial frequency axes, with periodicity determined by the beam sampling rates, and along the axial spatial frequency axis, with periodicity determined by the temporal sampling rate $f_{sample}$. Since the system is sampled, the previously mentioned relationships between the transmit aperture, the receive aperture, the effective aperture, the PSF and the coarray are replaced with their discrete equivalents.

Figure 6:
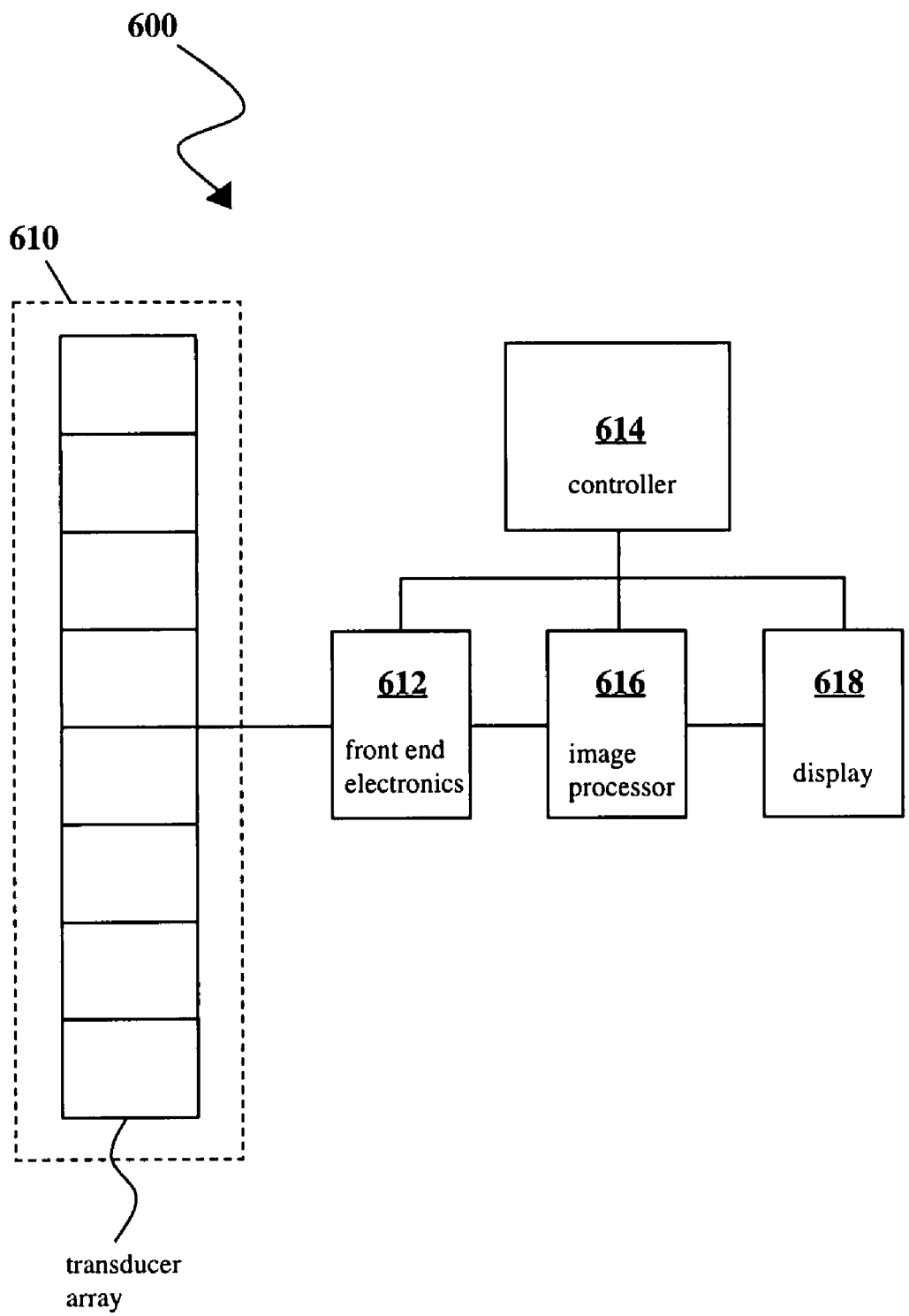
FIG. 6 is a block diagram illustrating the elements in an ultrasound imaging system according to the present invention.

FIG. 6 illustrates the principal components of an ultrasound imaging system 600 including a transducer array 610 and front-end electronics 612 for pulse generation, transmit/receive multiplexing, amplification, filtering, time-gain compensation, digital-to-analog conversion and transmit and receive beamforming. In addition, the ultrasound imaging system 600 contains a controller 614 such as a microprocessor and an image processor 616 including dynamic and static memory such as DRAM and SRAM for beam processing, envelope detection, scan conversion and log compression. The ultrasound imaging system 600 also contains a display 618. The controller 614 provides all the necessary timing and operation signals to the front-end electronics 612.

As is known in the art, transmit and receive beamforming are used to vary transmit and receive focal length and transmit and receive direction. Achieving dynamic transmit focusing requires multiple firings from the array 610 for each scan line, while dynamic receive focusing can be performed with only one firing. Since scan time per frame is limited in real-time imaging, transmit focus for FPA imaging is often fixed while receive focusing is performed dynamically. In an alternate embodiment, a plurality of images may be acquired for a plurality of transmit focal lengths. Each scan line is determined by selecting azimuth angle $\theta_1$ 518 and elevation angle $\theta_2$ 520 in FIG. 5. Energy in the ultrasound frequency range (2-50 MHz) is transmitting in that direction with a desired focal point by beamforming. Received response is processed by beamforming to shift the receive focal length dynamically. Coherent summation is performed to form the scan line, which has the received response at each receive focal length. A full set of scan lines is obtained by repeating these steps for all beam directions.

Figure 1:
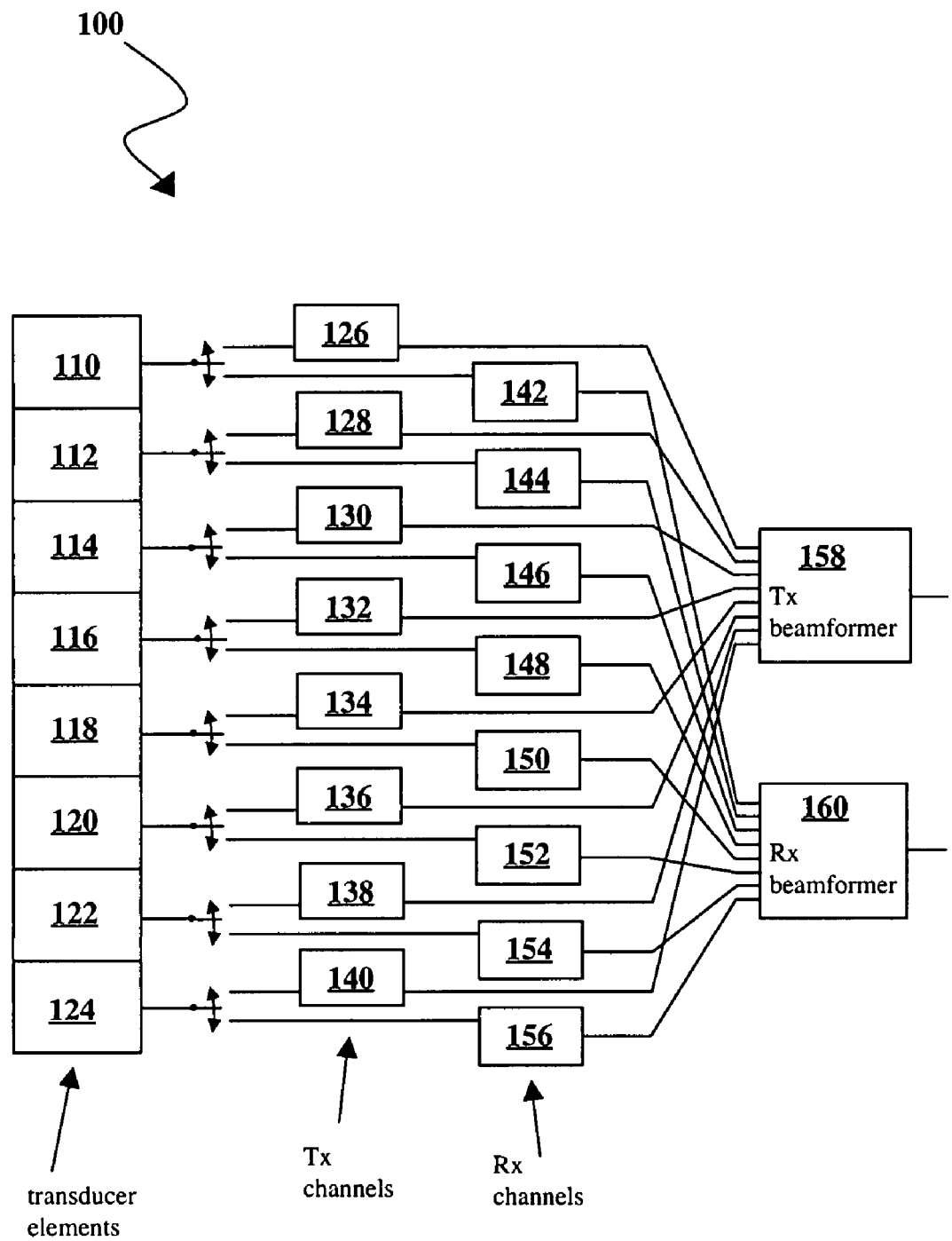
FIG. 1 is a diagram illustrating a full phased array (FPA) imaging system as described in the prior art.
Figure 2:
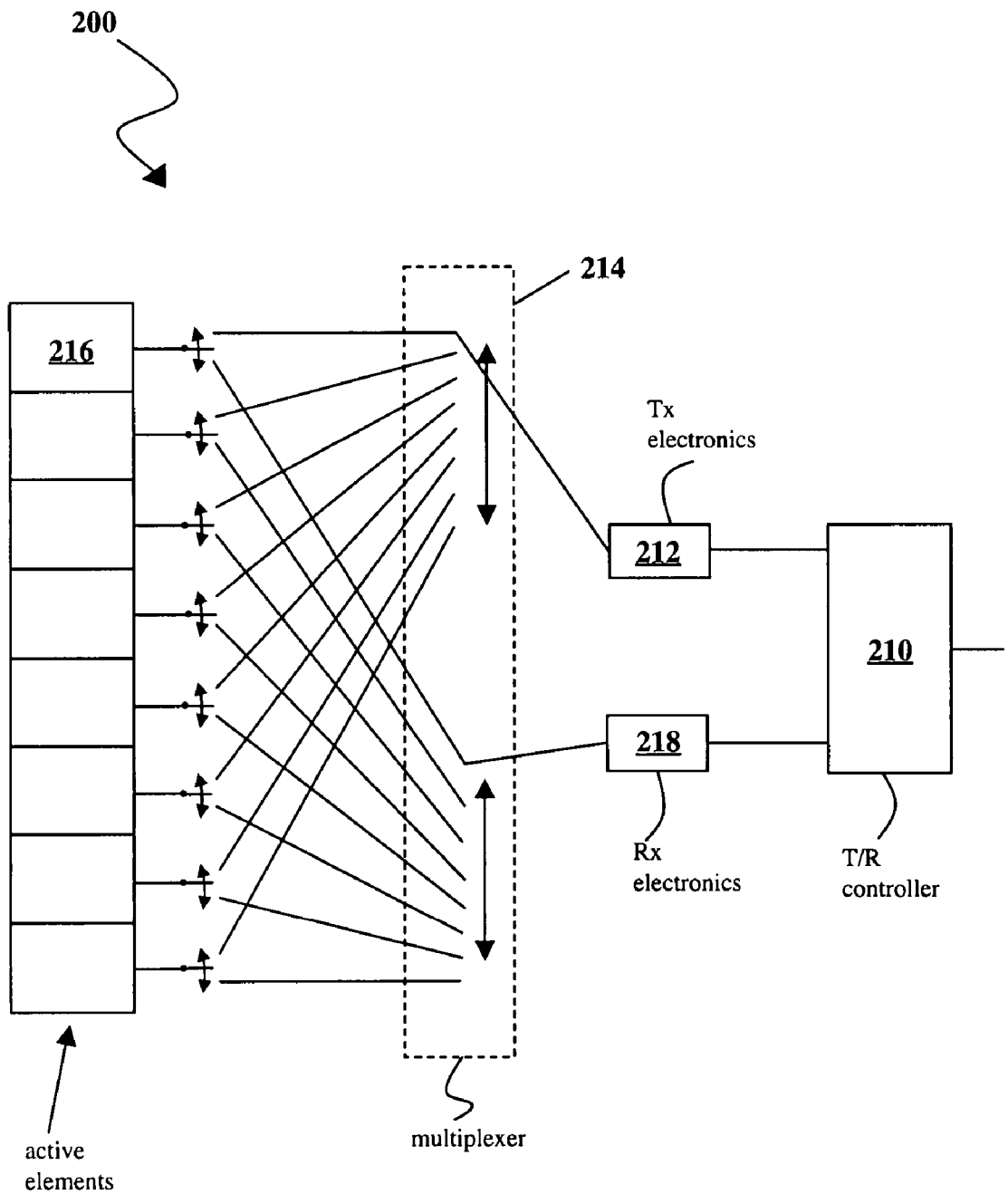
FIG. 2 is a diagram illustrating a classical synthetic aperture (CSA) imaging system and synthetic phased array (SPA) imaging as described in the prior art.
Figure 3:
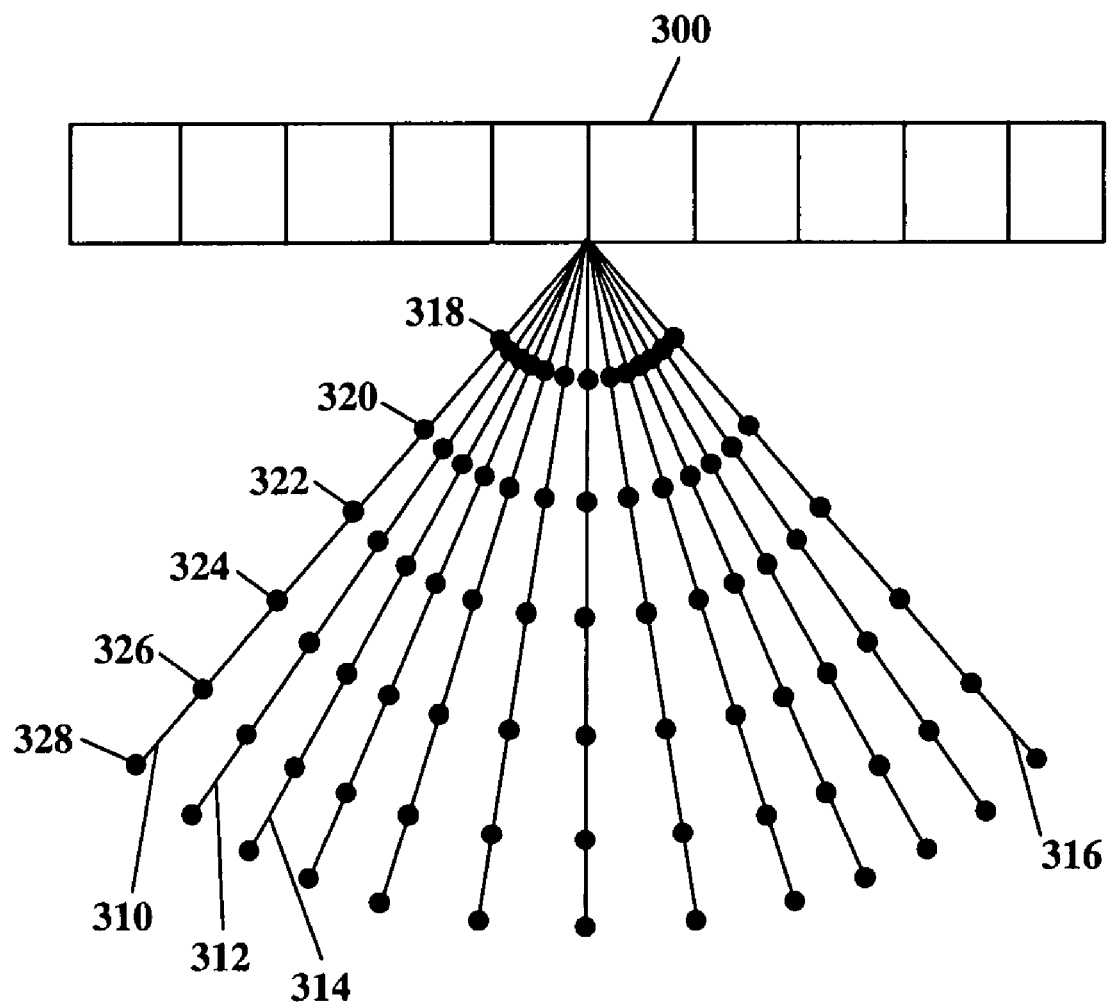
FIG. 3 is a diagram illustrating FPA imaging as described in the prior art.

FIG. 3 illustrates the process of determining scan lines for FPA imaging for an array 300 that corresponds to a 2D cross-section in the plane defined by the azimuth angle $\theta_1$ 518 or the elevation angle $\theta_2$ 520. Scan lines 310, 312, 314 up to 316 (corresponding to $Q_1$ or $Q_2$) are acquired in sequential steps. Each scan line 310, 312, 314 and 316 has data at receive focal lengths 318, 320, 322, 324, 326 and 328. As shown previously in FIG. 1, for multiple element transducer arrays FPA imaging requires an equivalent number of front-end processing channels. All elements are used during transmit and receive in order to form each of the $Q_1 \times Q_2$ beams.

Referring to FIG. 5, the imaging technique of this invention is based on $K_1 \times K_2$ subarrays each having multiple adjacent elements $M_1$ 528 and $M_2$ 530 in the transducer array 500. In this technique the subarrays transmit energy with frequencies in the ultrasound region and receive responses to this energy. The elements in active subarray 532 transmit and receive in parallel. Active subarray 532 is multiplexed across the full $N_1$ 510×$N_2$ 514 transducer array 500.

Since the subarray acquires a smaller range of lateral spatial frequencies than the full array, the beam space sampling requirements are relaxed. It is, therefore, possible to reduce the number of firings without loss of information in the image by sparsely sampling the beam space. The beam-space sampling criterion is dependent only on the active aperture size and not its relative location. To avoid aliasing, the beam sampling rate for PSA imaging with the $M_1$ 528×$M_2$ 530 active subarray 532 is $$Q_{S1} \geq \frac{4M_1 d_1}{\lambda_{min}} \sin\left(\frac{\Theta_1}{2}\right)$$

and $$Q_{S2} \geq \frac{4M_2 d_2}{\lambda_{min}} \sin\left(\frac{\Theta_2}{2}\right),$$

where $Q_{S1}$ and $Q_{S2}$ are the number of samples (beams) required in the first lateral direction 512 and the second lateral direction 516 for the active subarray 532. $Q_{S1}$ and $Q_{S2}$ are typically chosen to be the smallest integers that satisfy these equations. In this invention, the beam space is coarsely sampled to meet the sampling criteria for each transmit/receive subarray. The total number of beams for each active subarray 532 is equal to ($Q_{S1} \times Q_{S2}$). After multiplexing the active subarray 532 over the full transducer array 500, a total of $K_1 \times K_2$ sets of $Q_{S1} \times Q_{S2}$ beams are acquired. We refer to these as low-beam-rate subarray images, one for each subarray.

High-beam-rate subarray images correspond to the full set of $Q_1 \times Q_2$ beams, and are ideally equal to the images that would have been formed if each of the subarrays had directly acquired all $Q_1 \times Q_2$ beams. Increasing the beam density to reconstruct high-beam-rate subarray images from the low-beam-rate subarray images is accomplished by upsampling and interpolating in the planes corresponding to the azimuth angle 518 and the elevation angle 520. This may be performed in the image processor 616 shown in FIG. 6. In an alternate embodiment, upsampling and interpolation is varied for at least some of the subarrays. Typically, the interpolation is accomplished in at least a filter. Alternatively, null scan lines, having zeros for each receive focal length, are inserted between the beams in the low-beam-rate subarray image prior to applying an interpolation filter. Another implementation, is to upsample, apply the interpolation filter and then to discard samples to achieve the desired sample rate. The upsampling factors in the planes corresponding to the azimuth angle 518 and the elevational angle 520 must be chosen as $$L_1 \geq \frac{Q_1}{Q_{S1}}$$

and $$L_2 \geq \frac{Q_2}{Q_{S2}}.$$

Upsampling the subarray beams by more than this amount corresponds to oversampling relative to the number of beams in the final image, $Q_1$. No information is lost, but further upsampling, filtering, and downsampling are required to generate the desired image with $Q_1$ beams. Upsampling by less than this factor results in a loss of lateral spatial frequency information captured by the subarrays In general, $L_1$ and $L_2$ are chosen to be the smallest integers satisfying the equations above.

The reconstructed high-beam-rate subarray images are then combined to form the final high-beam-rate PSA image. This step may be accomplished by adding the high-beam-rate subarray image for each subarray to a running summator. In general, this step includes appropriate weighting of each of the high-beam-rate subarray images as well as subarray-dependent spectral modification. All of these steps may be performed in the image processor 616 in FIG. 6. With the proper choice of the filters and weights, the quality of the final image is comparable to that achieved using FPA imaging for receive image focal lengths near the transmit focal length. We refer to the imaging technique of this invention as phased subarray (PSA) imaging. It is distinct from CSA, SPA and FPA imaging. Note that the axial resolution is unaffected by PSA imaging.

Figure 7:
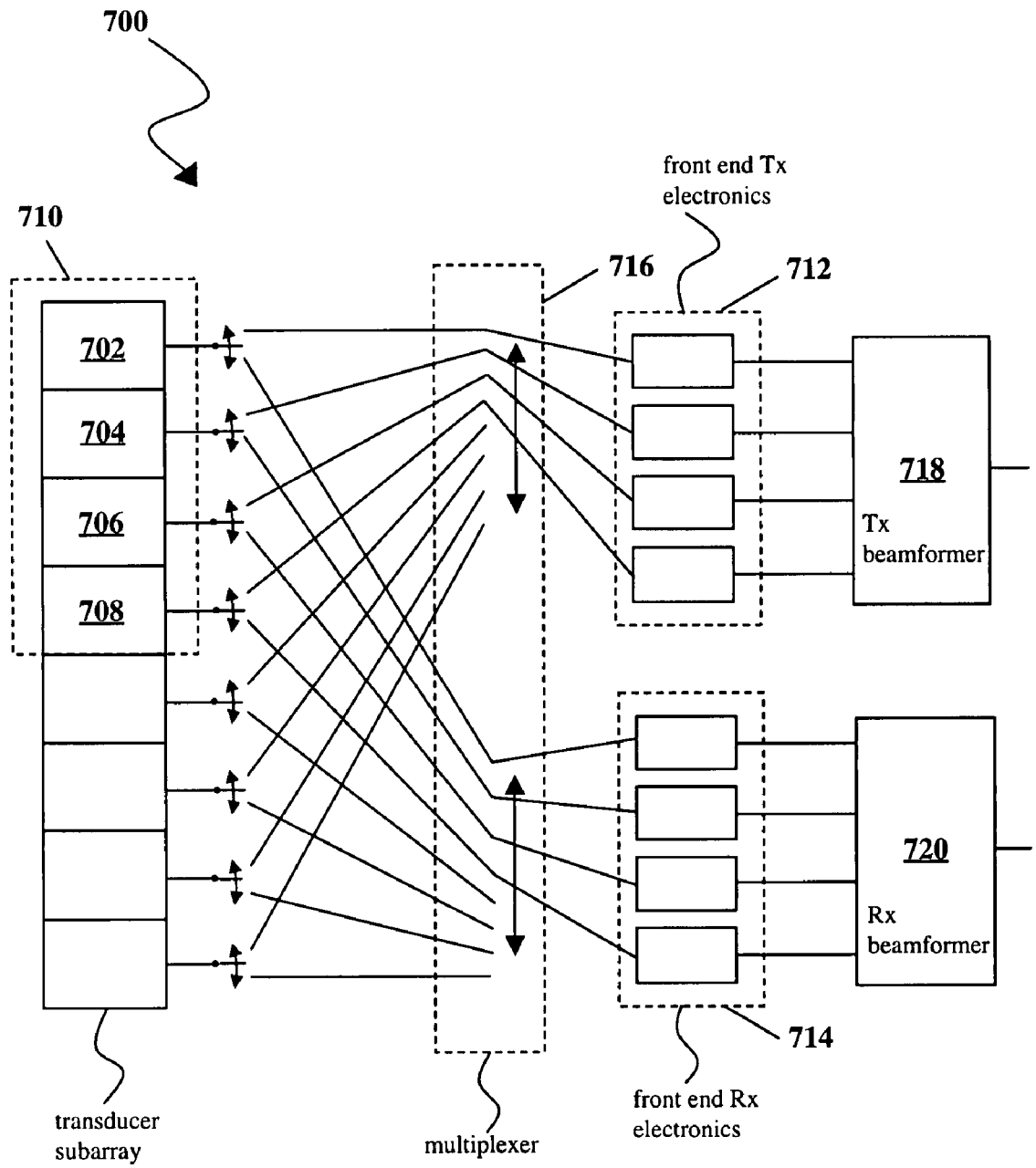
FIG. 7 is a diagram illustrating a PSA imaging system according to the present invention.

Referring to FIG. 6, the front-end electronics 612 complexity in PSA imaging depends directly upon the subarray size, ($M_1$ 528×$M_2$ 530 channels are required as shown in FIG. 5) motivating the choice to make the subarray size much smaller than the full array size, i.e., $M_1$ 528 much less than $N_1$ 510 and $M_2$ 530 much less than $N_2$ 514. FIG. 7 illustrates the front-end transmit 712 and receive electronics 714 of a PSA imaging system 700 with 4 elements 702, 704, 706, 708 in subarray 710 along the first lateral direction 512 or the second lateral direction 516 as defined in FIG. 5. Referring to FIG. 7, the subarray 710 is driven by drive signals from transmit beamformer 718 via the transmit electronics 712 and multiplexer 716. Receive signals from the subarray 710 are coupled to receive beamformer 720 via the receive electronics 714 and the multiplexer 716. In an alternate embodiment of the invention (not shown), one subarray is used for transmitting energy with frequencies in the ultrasound and a separate subarray is used for receiving the responses to the transmission of this energy.

Referring back to FIG. 5, in one embodiment of this invention each subarray has the same size $M_1$ 528×$M_2$ 530 and the subarrays are regularly spaced in first lateral direction 512 and second lateral direction 516. In another embodiment, each subarray is square, i.e., $M_1$ 528 and $M_2$ 530 are equal. Depending on the subarray geometry, the subarrays may overlap with one another in order to allow restoration of all spatial frequencies. Overlap 534 is defined as adjacent subarrays 532 and 536 having a number of adjacent elements in common. In general, the overlap along lateral directions 512 and 516 need not be the same. If PSA imaging is implemented with the same active subarray 532 for transmit and receive, adjacent, non-overlapping subarrays will cause nulls in the coarray that represent a complete loss of information at those spatial frequencies. Therefore, overlap 534 is required in this embodiment. In an alternate embodiment, where separate subarrays transmit and receive, adjacent and touching subarrays are sufficient to prevent nulls in the coarray.

In addition to the number of samples (beams) that are acquired, the number of firings required for PSA imaging depends on subarray size, $M_1$ 528×$M_2$ 530, and the number of subarrays, $K_1$×$K_2$, needed to cover the entire transducer array 500 without a loss of information. This provides an additional motivation for keeping the subarray size small. However, to increase the frame rate, which is inversely proportional to the number of firings, the number of subarrays should be kept to a minimum. For a fixed transducer array 500 size and fixed subarray size 532, decreasing the number of subarrays also implies decreasing the amount of overlap 534 between subarrays.

In general, for an arbitrary amount of overlap 534 (as well as for arbitrary subarray size $M_1$ 528 and $M_2$ 530, arbitrary spacing $d_1$ 524 and spacing $d_2$ 526 in the array 500, and arbitrary subarray and full array 500 aperture functions) the summation of the high-beam-rate subarray images results in an irregularly shaped effective aperture function and is not suitable for imaging. Therefore, one embodiment of this invention includes additional filtering to spectrally modify the high-beam-rate subarray images to produce a more uniform spatial frequency response and to restore the coarray for the final high-beam-rate PSA image to that of an FPA image. This restoration filtering may be combined with the interpolation filter. The step of weighing each of the high-beam-rate subarray images may also be combined with this restoration filtering. In general, the restoration filter is varied for the subarrays. In an alternate embodiment of this invention, the restoration filter is also varied for the receive focal lengths.

The interpolation filtering, and the restoration filtering may be implemented in a single filter or in separate filters. The filter may be analog or digital. For a digital filter, settings for the taps corresponding to filters for different subarrays may be stored in a look-up table. In an alternate embodiment, some of the settings for a digital filter may be calculated using the controller 614 in FIG. 6 based on values stored in a look-up table (not shown). The filter may be determined by a modification of the optimization technique known in the art in which a stop band weighting function is defined, a pass band weighting function is defined and a multiple-objective weighting parameter is defined. The desired filter is then determined by minimizing the sum of the squared error between desired coarray and reconstructed coarray for all the subarrays and the multiple-objective weighting parameter times the sum of the squared out-of-band (or stop band) energy for all the subarrays.

Since the filter must already be applied to all the low-beam-rate subarray images that are used to form the final high-beam-rate PSA image, additional filtering capabilities may be combined with the filter to address further image enhancement at no extra cost. In an alternate embodiment of the present invention, images may be further enhanced by filtering to correct for temporal spectral imperfections, for defocusing for receive focal lengths outside of the focal zone corresponding to the transmit focal length and to compensation for a non-uniform spatial frequency response.

Images from narrowband systems can use a filter with support only in the lateral directions 512 and 516 in FIG. 5, and can have minimal support in the axial direction 522. Wideband systems also require filter support in the axial direction 522 in order to properly reconstruct high-beam-rate subarray images from their low-beam-rate counterparts. Therefore, in another embodiment, for sufficiently narrowband signals the filter or filters for interpolation and spectral modification (including restoration) is a 1D or 2D filter for 2D or 3D imaging, respectively. In yet another embodiment, for wideband signals the filter or filters for interpolation and spectral modification (including restoration) is a 2D or 3D filter for 2D or 3D imaging, respectively.

Figure 4:
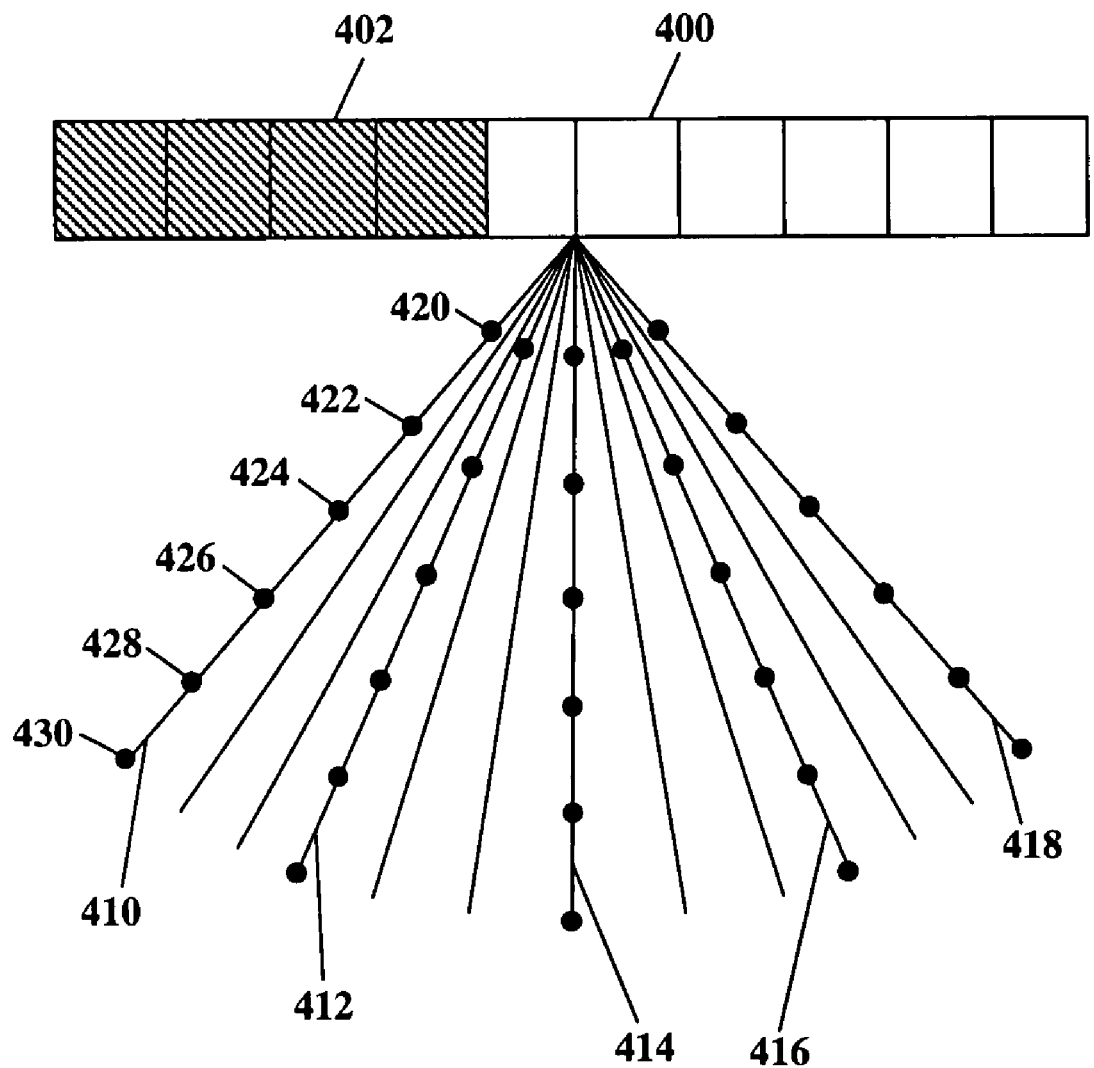
FIG. 4 is a diagram illustrating phased subarray imaging (PSA) according to the present invention.

FIG. 4 illustrates the process of determining scan lines for PSA imaging for a 2D cross-section in the plane defined by the azimuth angle $\theta_1$ 518 or the elevation angle $\theta_2$ 520 in FIG. 5. Referring back to FIG. 4, scan lines 410, 412, 414, 416 and 418 (corresponding to $Q_{S1}$ or $Q_{S2}$) are acquired in sequential steps by active subarray 402 to produce the low-beam-rate subarray image. Each scan line 410, 412, 414, 416 and 418 has data at receive focal lengths 420, 422, 424, 426, 428 and 430. The active subarray 402 is multiplexed across array 400. Each subarray acquires one of scan lines 410, 412, 414, 416 and 418 before the next scan line is acquired. In an alternate embodiment, it is possible for each of the subarrays to acquire one of scan lines 410, 412, 414, 416 and 418 consecutively. However, this embodiment is not preferred since it results in a longer time between the acquisition of scan lines 410, 412, 414, 416 and 418 by each of the subarrays and leads to motion artifacts. The low-beam-rate subarray images are then interpolated in a filter. The resulting high-beam-rate subarray images are weighted prior to summation to produce a high-beam-rate PSA image.

The SNR of an array imaging system is dependent upon the number of active transmit and receive channels. Assuming that the noise is additive and statistically independent on the receive channels, the normalized SNR in dB of the PSA imaging system with $M_1=M_2=M$ is given by $$SNR = 20\log\left[M\sqrt{M}\,\frac{\sum_k b[k]}{\sqrt{\sum_k b^2[k]}}\right] + SNR_o,$$

where b[k] is the weighting of the k-th high-beam-rate subarray image, $SNR_0$ is the pulse-echo SNR of a single channel, assuming that the SNR of the array channels are identical. Referring to FIG. 5, as an example for $M_1$ 528×$M_2$ 530=4×4, $N_1$ 510×$N_2$ 514=16×16 and $K_1$×$K_2$=5×5, the normalized SNR values of the FPA, PSA and SPA imaging systems are 72, 60 and 48 dB, respectively. Table I shows a comparison of the relative theoretical performance of FPA, PSA and SPA imaging systems for square arrays ($N_1$ 510=$N_2$ 514=N, $M_1$ 528=$M_2$ 530=M, $K_1$=$K_2$=K, and sector angles $\Theta_1$=$\Theta_2$=$\Theta$) with no additional restoration or spectral modification filtering besides a bandpass filter. While the SNR performance of PSA imaging is good, in another embodiment high-beam-rate subarray images for active subarray 532 may be acquired a plurality of times and averaged to improve the SNR. In yet another embodiment, low-beam-rate subarray images for active subarray 532 may be acquired a plurality of times and averaged to improve the SNR prior to interpolation.

TABLE 1

Performance comparison of FPA, PSA and SPA imaging.

| | Number of Firings | |
|---|---|---|
| Algorithm | Exact | Numerical Example (N = 32, M = 8, K = 7, $\Theta$ = 90°, d = $\lambda_{min}/2$) |
| SPA | $N^4$ | 1048576 |
| FPA | $\left[\frac{4Nd}{\lambda_{min}}\sin\left(\frac{\Theta}{2}\right)\right]^2$ | 2048 |
| PSA | $\left[\frac{4KMd}{\lambda_{min}}\sin\left(\frac{\Theta}{2}\right)\right]^2$ | 6272 |

| | Front-end Hardware Complexity | |
|---|---|---|
| Algorithm | Exact | Numerical Example (N = 32, M = 8, K = 7, $\Theta$ = 90°, d = $\lambda_{min}/2$) |
| SPA | 1 | 1 |
| FPA | $N^2$ | 1024 |
| PSA | $M^2$ | 64 |

| | Signal-to-Noise Ratio (SNR) in dB | |
|---|---|---|
| Algorithm | Exact | Numerical Example (N = 32, M = 8, K = 7, $\Theta$ = 90°, d = $\lambda_{min}/2$) |
| SPA | $20\log_{10}(N^2)$ | 90 |
| FPA | $20\log_{10}(N^3)$ | 90 |
| PSA | $20\log_{10}\left[M^3\left(\frac{\sum_k b[k]}{\sqrt{\sum_k b^2[k]}}\right)^2\right]$ | 69 |

Example 1

For the special case of a fixed number of adjacent elements in each subarray and a fixed overlap 534 in FIG. 5 equal to half the number of adjacent elements $M_1$ 528 or $M_2$ 530 along lateral directions 512 or 516 in each subarray, the filter for interpolation is merely a bandpass; no additional spectral modification in a restoration filter is required. For narrowband imaging, the bandpass is 1D. For wideband imaging, the bandpass is in general 2D. The final high-beam-rate PSA image is a linear combination of individual high-beam-rate subarray images. For a 2D cross-section in the plane defined by the azimuth angle $\theta_1$ 518 or the elevation angle $\theta_2$ 520, the weight b[k] applied to the high-beam-rate subarray image corresponding to $k^{th}$ subarray is given by $$b_1[k] = \left(\frac{K_1+1}{2}\right) - \left|k - \left(\frac{K_1-1}{2}\right)\right|,$$

where k is between 0 and $K_1-1$. For this geometry, and more generally for overlap 534 less than half the number of adjacent elements $M_1$ 528 or $M_2$ 530, the frame rate reduction will never exceed a factor 2 in 2D and a factor of 4 in 3D.

Figure 10A:
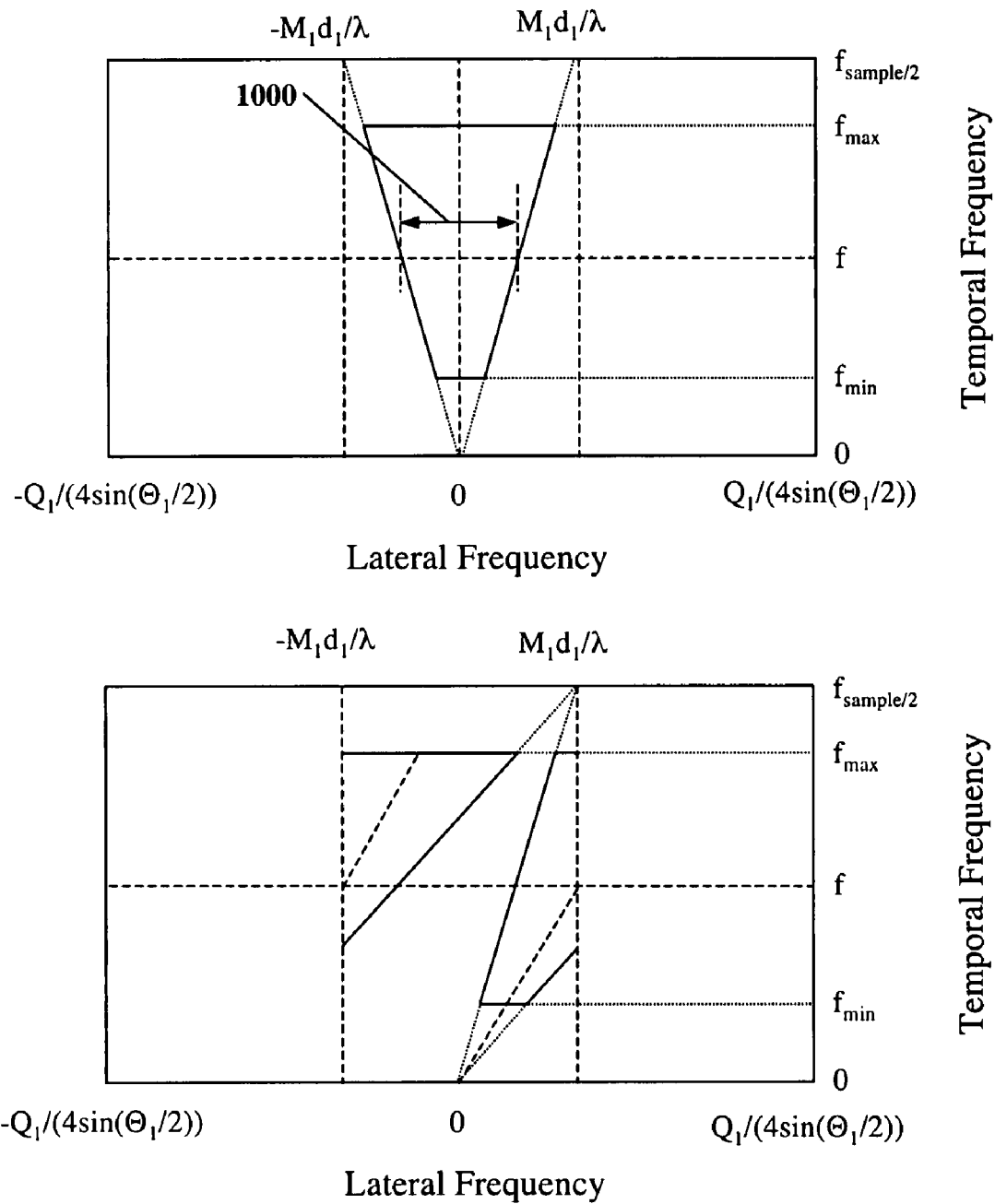
FIG. 10a is a diagram illustrating the spatial frequency response in PSA imaging according to the present invention.
Figure 10B:
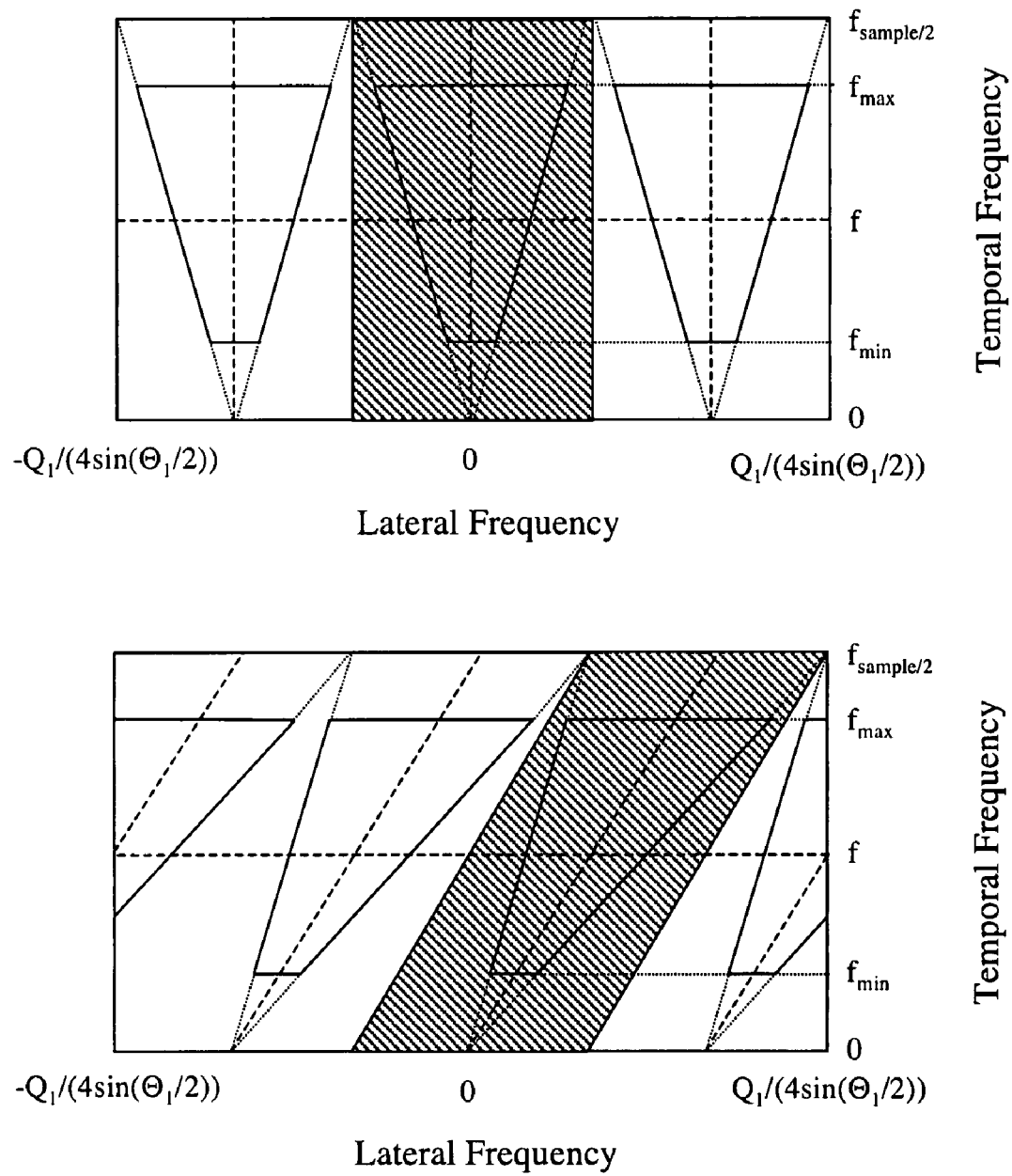
FIG. 10b is a diagram illustrating the spatial frequency response in PSA imaging according to the present invention.
Figure 10C:
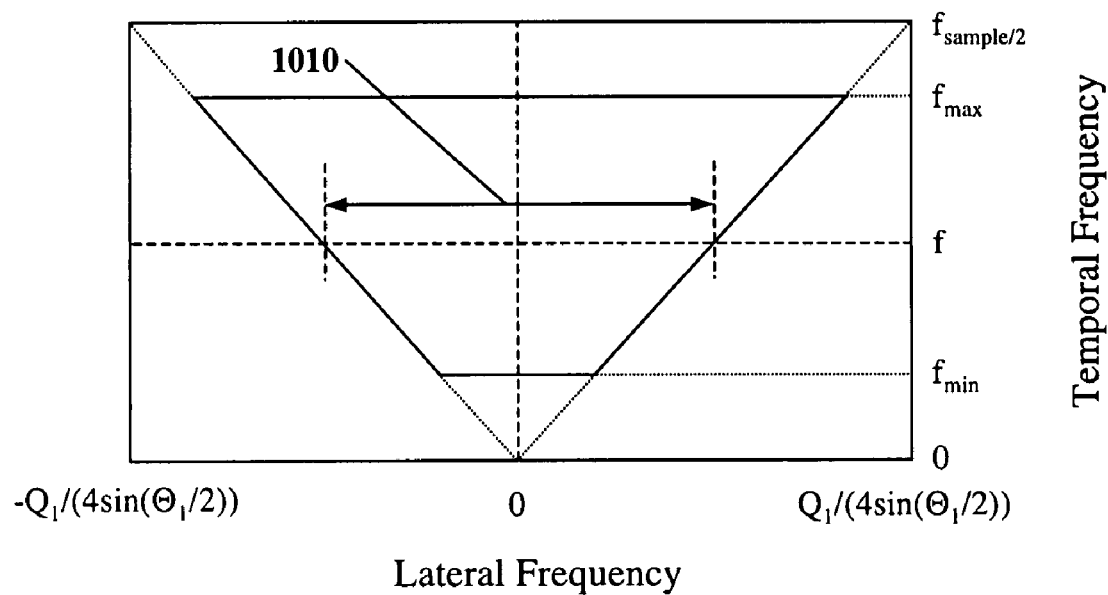
FIG. 10c is a diagram illustrating the spatial frequency response in PSA imaging according to the present invention.

FIG. 10a-c illustrates the 2D lateral and axial spatial frequency response for PSA imaging corresponding to a cross-section of 3D data in the plane defined by the azimuth angle $\theta_1$ 518 or elevation angle $\theta_2$ 520 in FIG. 5. For convenience, take the plane defined by the azimuth angle $\theta_1$ 518. In this example, $K_1$=7 subarrays span all $N_1$ 510 elements in FIG. 5. Each subarray is composed of $M_1$ 528=0.25×$N_1$ 510 elements. The subarrays overlap 534 by 0.125×$N_1$ 510 elements. The number of beams in the subarray images is equal to one-third the number of beams in the final image ($Q_1/Q_{S1}$=3).

The horizontal and vertical axes in FIG. 10a-c are the lateral and temporal frequency, respectively. Note that the axial spatial frequency and the temporal frequency are related by the speed of sound. The projection of the spatial frequency response onto the temporal frequency axis is equal to the Fourier transform of the pulse response. Note that the spatial frequency response in FIG. 10a-c for subarrays that are not at the center of the array 500 in FIG. 5 are sheared, where the shear factor is proportional to the distance of the respective subarray from the center of the array.

The process of converting the real received signal to a complex-valued analytic signal eliminates all negative temporal frequency components of the signal. The effect on k-space is that there is no signal contribution for temporal frequency less than zero. Therefore, the corresponding bottom half of the illustration in FIG. 10a-c is not shown.

FIG. 10a-c shows the theoretical nonzero portions of the 2D spatial frequency response at each stage of the image acquisition and formation process. The first step is to acquire $Q_S$ beams from each of the $K_1$ subarrays. By reducing the number of directly acquired beams the frame rate is only reduced by less than a factor of 2. Two spatial frequency responses for these low-beam-rate subarray imaging systems are shown in FIG. 10a. The top illustration corresponds to a subarray at the center of the array and the lower illustration to an off-center subarray. The lateral frequency width 1000 of both spatial frequency response is $2M_1 d_1/\lambda$. The next step is to upsample these images by inserting zero-valued beams between the acquired beams. The total number of beams in the upsampled images is the same as that in the FPA system, i.e., $Q_1$. The spatial frequency response after upsampling is shown in FIG. 10b. These spatial frequency responses represent the periodic replication of the low-beam-rate spatial frequency responses shown in FIG. 10a. In this example, the high-beam-rate subarray images are obtained by applying a bandpass filter. The passband of such a filter is shown by the striped background in FIG. 10b. This filter can be applied by convolution in the spatial domain or by multiplication in the spatial frequency response domain. The filter effectively suppresses the replicas of the original spatial frequency response; no restoration filter is required. After coherent weighting and summation of all 7 high-beam-rate subarray images, the spatial frequency response becomes comparable to that of FPA imaging (see FIG. 10c) with a lateral frequency width 1010 equal to $2N_1d_1/\lambda$.

Example 2

Figure 8:
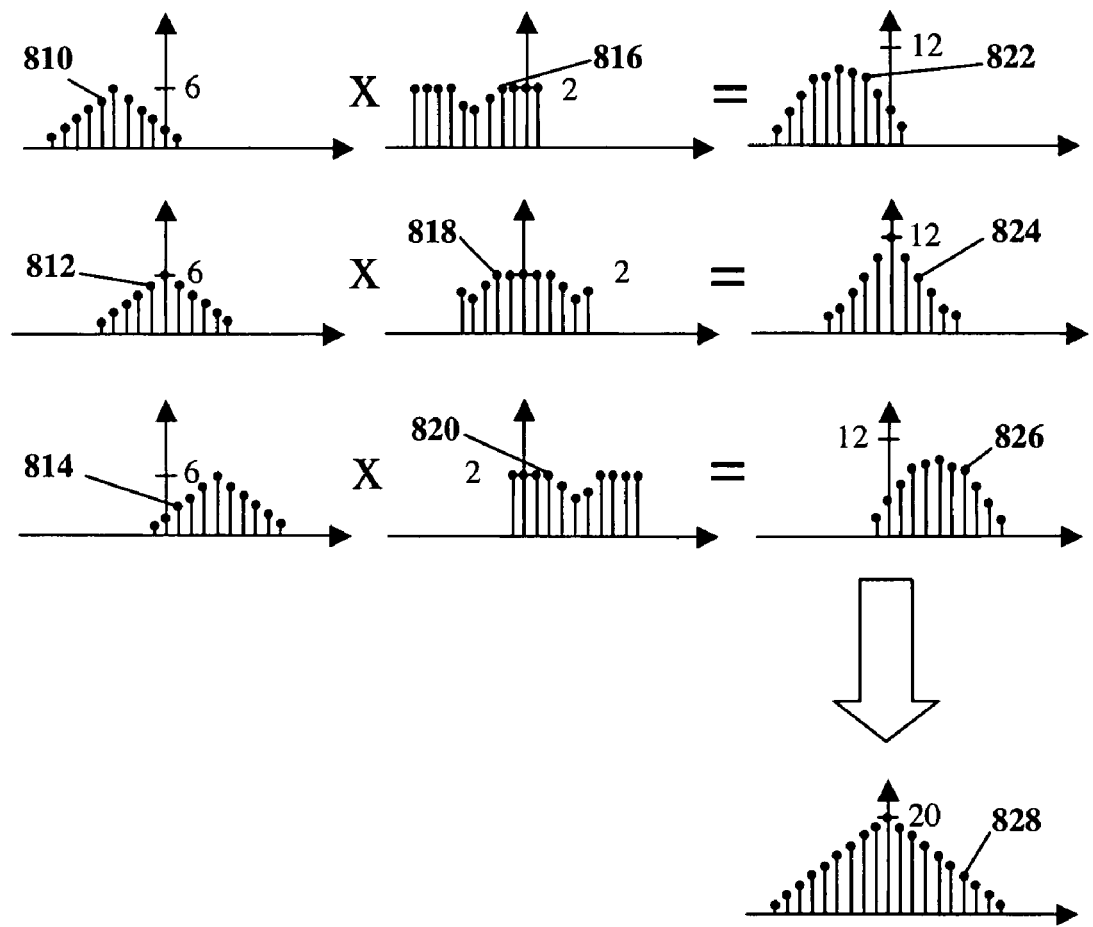
FIG. 8 is a diagram illustrating restoration filtering in PSA imaging according to the present invention.

FIG. 8 illustrates the impact of restoration filters including the subarray weights on the high-beam-rate PSA coarray. FIG. 8 shows the coarray corresponding to a 1D lateral cross-section of 3D data in the plane defined by the azimuth angle $\theta_1$ 518 or elevation angle $\theta_2$ 520. In this example, $N_1$ 510 or $N_2$ 514=10, $M_1$ 528 or $M_2$ 530=6 and $K_1$ or $K_2$=3 in FIG. 5. Referring back to FIG. 8, coarrays 810, 812 and 814 each correspond to a subarray. Each coarray 810, 812 and 814 has 11 non-zero samples (2 $M_1$ 528-1 or 2$M_2$ 530-1). Without restoration filtering, the weighted sum of coarrays 810, 812 and 814 results in an unrestored PSA coarray (not shown) that is not suitable for producing a high-beam-rate image. One possible set of restoration filters 816, 818 and 820 that could be used to obtain a high-beam-rate PSA coarray 828 that is comparable to a FPA coarray are shown. In this illustration, all the weights are equal to 2, and are incorporated into the magnitudes of the restoration filters 816, 818 and 820. The products of the coarrays 810, 812 and 814 with the restoration filters 816, 818 and 820 produce restored coarrays 822, 824 and 826. The sum of these restored coarrays 822, 824 and 826 is the desired high-beam-rate PSA coarray 828 in the plane defined by the azimuth angle $\theta_1$ 518 or elevation angle $\theta_2$ 520 in FIG. 5. PSA coarray 828 has 19 non-zero samples (2 $N_1$ 510-1 or 2$N_2$ 514-1)

Example 3

Figure 9A:
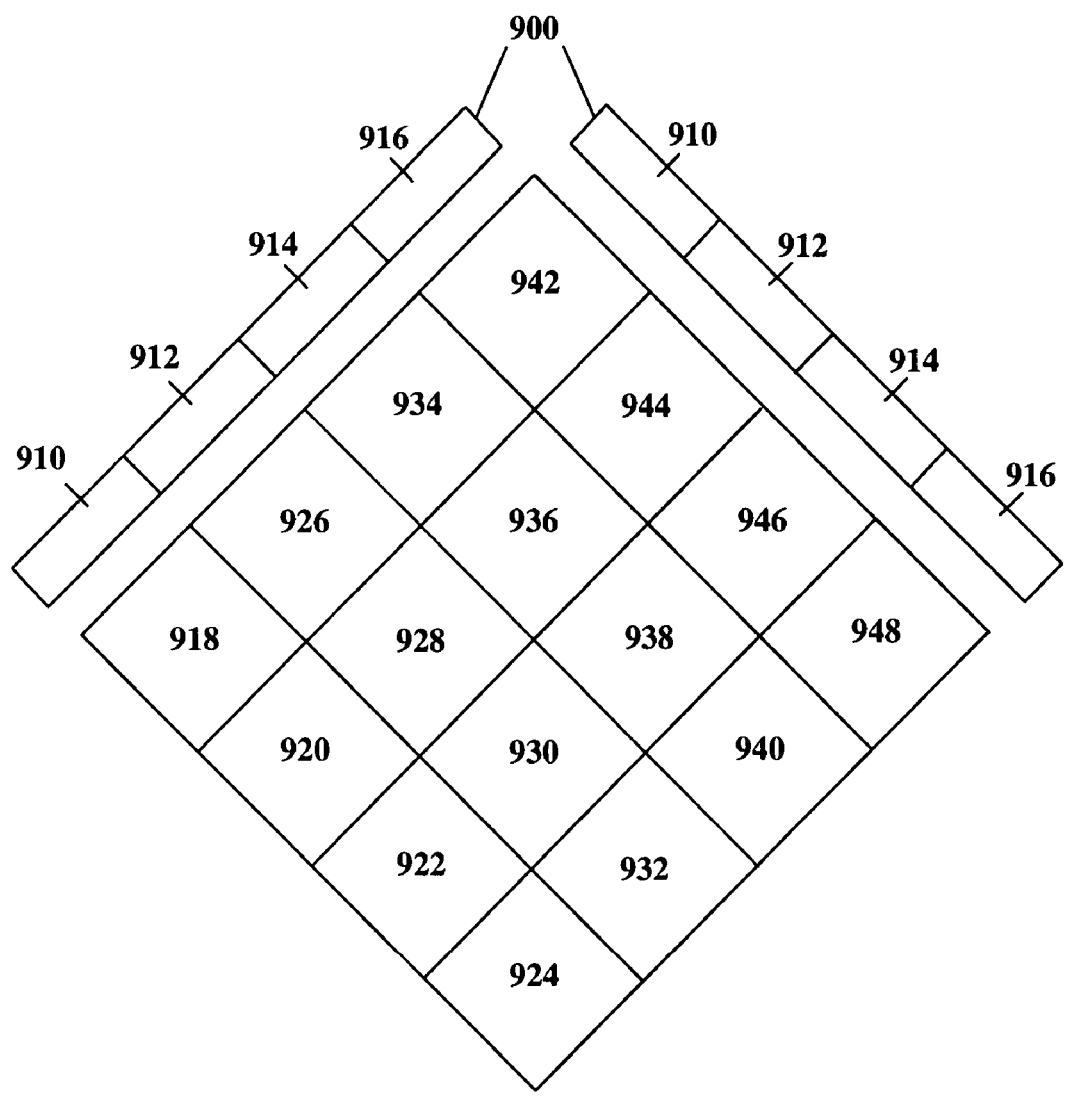
FIG. 9a is a diagram illustrating the comatrix for PSA imaging according to the present invention.
Figure 9B:
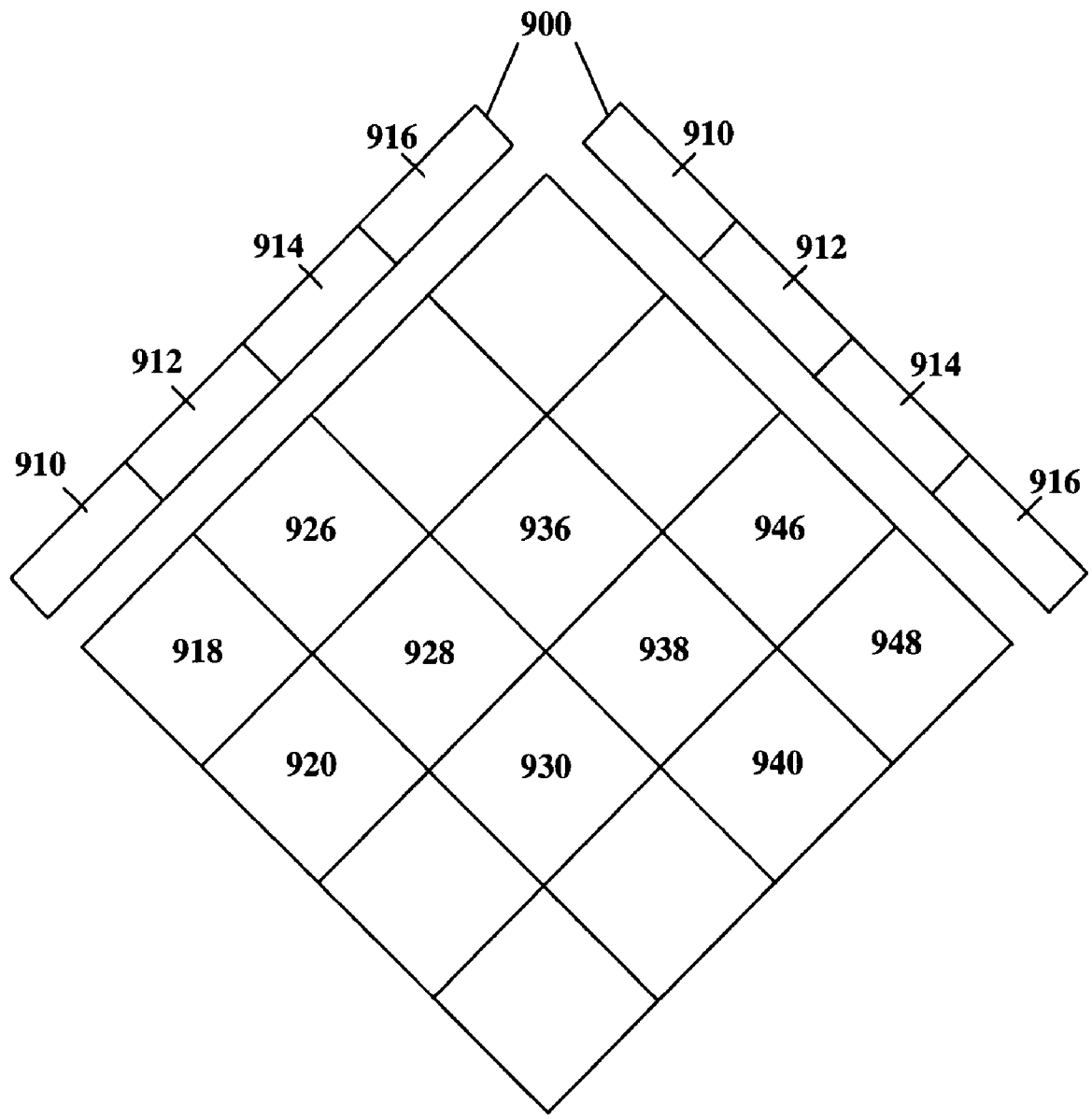
FIG. 9b is a diagram illustrating the comatrix for PSA imaging according to the present invention.

A comatrix serves as a useful tool for choosing which transmit and receive subarrays should be used to form the final coarray. Two example comatrices are shown in FIG. 9a-b, all with $N_1$ 510 or $N_2$ 514=16 and $M_1$ 528 or $M_2$ 530=4 (once again, FIG. 9a-b illustrates a 2D cross-section in the plane defined by the azimuth angle $\theta_1$ 518 or elevation angle $\theta_2$ 520 in FIG. 5). Each example demonstrates how different choices for the number of subarrays and the transmit/receive subarray combinations affect the restoration filter needed to achieve an FPA-comparable coarray.

For the example shown in FIG. 9a, the array 900 is divided into four non-overlapping, adjacent subarrays 910, 912, 914 and 916. Images are acquired using 16 permutations 918, 920, 922, 924, 926, 928, 930, 932, 934, 936, 938, 940, 942, 944, 946 and 948 of the subarrays 910, 912, 914 and 916, one for every transmit/receive combination. The weights used in summing the coarrays for permutations 918, 920, 922, 924, 926, 928, 930, 932, 934, 936, 938, 940, 942, 944, 946 and 948 are all 1, i.e., weighting is not required in this configuration. The comatrix is fully-populated and equivalent to the comatrix for FPA or SPA imaging. In this configuration, the resulting coarray (not shown) is comparable to that of FPA without any restoration filtering. The disadvantage of this configuration is that each beam must be acquired 16 times. The frame rate can be improved by reducing the number of active transmit/receive subarray combinations.

For the example shown in FIG. 9b, the same subarrays 910, 912, 914 and 916 are employed, but only 10 transmit/receive subarray combinations are used (918, 920, 926, 928, 930, 936, 938, 940, 946 and 948). Combining the coarrays without filtering or weights would result in non-uniform coarray (not shown). Fortunately, the desired FPA-comparable coarray is a linear combination of the coarrays, with weights of 1, 1, 1, 3, 2, 2, 3, 1, 1 and 1 for combinations 918, 920, 926, 928, 930, 936, 938, 940, 946 and 948, respectively.

Other geometries with overlap 534 and different permutations of transmit/receive combinations (not shown) reduce the number of firing events per beam required to obtain the coarray. For each geometry and the transmit/receive combinations selected in the comatrix, different weights are required to obtain the FPA-comparable coarray. Some geometries with overlap 534 require restoration filtering to obtain the FPA-comparable coarray. If $N_1$ 510 or $N_2$ 514=16, $M_1$ 528 or $M_2$ 530=4, $K_1$ or $K_2$=7, overlap 534=2 (half of $M_1$ 528 or $M_2$ 530) and the same subarray is used to transmit and receive, no restoration filtering is required (this example corresponds to the conditions in Example 1). In this case, only one firing is performed per subarray, since each subarray is acting as both transmitter and receiver. The appropriate weights starting at one side of the array 900 and moving to the other side are 1, 2, 3, 4, 3, 2 and 1. If $N_1$ 510 or $N_2$ 514=16, $M_1$ 528 or $M_2$ 530=4, $K_1$ or $K_2$=5, overlap 534=1 and the same subarray is used to transmit and receive, restoration filtering is required to reshape the coarrays in such a way that they can be linearly combined to form the desired final FPA-comparable coarray. Thus, the number of firings per beam was decreased further by reducing the amount of overlap 534 between adjacent subarrays at the expense of requiring restoration filtering.

Example 4

Additional analysis and measurements of PSA imaging have been performed. In the analysis and measurements:
$N_1$ 510=128 and $N_2$ 514=1;
spacing $d_1$ 524 (250 microns in the measurements) is equal to half of the minimum wavelength;
in the analysis, the temporal sampling frequency was equal to 96 MHz, the pulse center frequency was 3 MHz and, after beamforming, the temporal sampling rate was 12 MHz;
in the measurements, the temporal sampling frequency was 50 MHz, the pulse center frequency was 3 MHz and, after beamforming, the temporal sampling rate was 12 MHz;
80% signal bandwidth;
$M_1$ 528=32;
$K_1$=7;
$Q_{S1}$ equal to 127 beams;
Q equal to 511;
transmit focal length in the measurements of 13 cm;
sector angle $\Theta_1$ in the measurements of 90°;
and the reconstruction filter was 2D with 31×31 taps.
The experimental data was acquired using a capacitive micromachined ultrasound transducer array imaging several thin wires placed in vegetable oil. The experimental set-up is further described in Ö. Oralkan et al, "Capacitive Micromachined Ultrasonic Transducers: Next Generation Arrays for Acoustic Imaging?," *IEEE Trans. Ultrason., Ferroelect., Freq. Contr.*, vol. 49, pp. 1596-1610 (2002). The analysis and experimental results are further described in Jeremy A. Johnson et al., "Coherent Array Imaging Using Phased Subarrays—Part I: Basic Principles," *IEEE Trans Ultrason, Ferroelec, and Freq Control*, vol. 52, no. 1, pp. 37-50, 2005, and Jeremy A. Johnson et al., "Coherent Array Imaging Using Phased Subarrays—Part I: Simulations and Experimental Results," *IEEE Trans Ultrason, Ferroelec, and Freq Control*, vol. 52, no. 1, pp. 51-64, 2005, the contents of which are incorporated by reference. Good agreement between simulated and measured PSF and coarray at each step in PSA imaging was found. In the experiments, the resultant high-beam-rate PSA B-scan images of a phantom wire were in good agreement with the FPA B-scan images.

Both the simulated and experimental results demonstrate the success of the invention for a particular choice of imaging parameters. In this case, the number of dedicated front-end hardware channels needed for both transmit and receive was reduced by a factor of 4, from 128 to 32. Compared to FPA imaging, this example decreases the frame rate by 43%.

PSA imaging has largely been described for the case of 3D imaging with a 2D transducer array. However, as illustrated in Example 4, PSA imaging may be applied to 2D ultrasonic imaging with a 1D transducer array with $N_2$ 514 in FIG. 5 equal to 1. In this embodiment, for sufficiently narrowband signals the filter or filters for interpolation and spectral modification (including restoration) is a 1D filter. For wideband signals in this embodiment, the filter or filters for interpolation and spectral modification (including restoration) is a 2D filter.

In ultrasound imaging, the received ultrasound signals are amplitude modulated about a carrier. In one embodiment of this invention, high-beam-rate PSA imaging is applied to the received signals before converting to baseband. In an alternative embodiment of this invention, the received signals are converted to baseband before high-beam-rate PSA imaging is applied. In yet another alternative embodiment of this invention, the received signals are converted to an intermediate frequency before high-beam-rate PSA imaging is applied.

The high-beam-rate PSA image method may be applied to real-valued receive signals. In this embodiment, the filters employed in PSA imaging are, in general, complex. In another embodiment, a Hilbert transform is applied to the real-valued receive signals to generate complex signals and the filters employed in PSA imaging are real.

The method can also be applied to many variations that have not been described here, such as uneven spacing $d_1$ 524 and spacing $d_2$ 526 in FIG. 5, non-uniform beam sampling as well as non-uniform or apodized apertures.

The above description has assumed that a transducer array 500 in FIG. 5 was used for forming images from acoustic waves. However, the theory applies to any coherent array imaging system, and is applicable to areas such as radar, optics, sonar, radio astronomy, seismic imaging, and other imaging modalities.

In view of the above, it will be clear to one skilled in the art that the above embodiments may be altered in many ways without departing from the scope of the invention. Accordingly, the scope of the invention should be determined by the following claims and their legal equivalents.

What is claimed is:

1. An imaging system, comprising:
   a) a plurality of subarrays, each having adjacent transducer elements, defining an array of transducers for transmission of energy in a plurality of transmit directions with at least one transmit focal length, for reception of responses to said energy and for output of receive signals;
   b) a subarray-dependent first filter for spectral modification and interpolation between scan lines for a plurality of receive directions, $Q_S$, and receive focal lengths from each of said subarrays; and
   c) a unit for combining outputs from said first filter corresponding to each of said subarrays to produce an image; wherein a number of receive directions $Q_{S1}$ in a first plane satisfies $$Q_{S1} \geq \frac{4M_1 d_1}{\lambda_{min}} \sin\left(\frac{\Theta_1}{2}\right),$$

where $M_1$ is a number of said adjacent transducer elements in a first dimension of each of said subarrays and said array, $d_1$ is a spacing between each of said adjacent transducer elements in said first dimension, $\lambda_{min}$ is a minimum wavelength in said transmitted energy, $\Theta_1$ is a first sector angle in said first plane, and wherein an upsampling ratio $L_1$ in said first plane during interpolation in said first filter satisfies $$L_1 \geq \frac{\frac{4N_1 d_1}{\lambda_{min}} \sin\left(\frac{\Theta_1}{2}\right)}{Q_{S1}},$$

where $N_1$ is a total number of said transducer elements in said array in said first dimension.

2. The image system of claim 1 further comprising a resampler for inserting null scan lines for additional directions between said receive directions for said scan lines from each of said subarrays, wherein said null scan lines are comprised of a set of zeros corresponding to each of said receive focal lengths.

3. The apparatus of claim 1 further comprising a first array of transducers for transmission of said energy and a second array of transducers for reception of said responses to said energy, wherein said first array is divided into said plurality of subarrays each having adjacent transducer elements, defining said first array.

4. The apparatus of claim 1 further comprising a first array of transducers for transmission of said energy and a second array of transducers for reception of said responses to said energy, wherein said second array is divided into said plurality of subarrays, each having adjacent transducer elements, defining said second array.

5. The apparatus in claim 1 wherein a first subarray transmits said energy and a second subarray receives said responses to said energy.

6. The apparatus in claim 1 wherein a first subarray transmits said energy and said first subarray receives said responses to said energy.

7. The apparatus of claim 1 wherein each of said subarrays has same number of said adjacent transducer elements.

8. The apparatus of claim 1 wherein each of said subarrays overlaps adjacent subarrays thereby having transducer elements in common with said adjacent subarrays.

9. The apparatus of claim 8 wherein said overlap of said subarrays is a fixed number of said adjacent transducer elements in each of said subarrays.

10. The apparatus in claim 1 further comprising a look-up table with settings for said first filter for at least some of said subarrays.

11. The apparatus of claim 10 further comprising a calculating unit for determining at least some settings for said first filter for at least some of said subarrays.

12. The apparatus of claim 1 wherein said first filter is selected from the group consisting of a 1-dimensional filter, a 2-dimensional filter and a 3-dimensional filter.

13. The apparatus of claim 1 wherein said first filter is varied for at least one of said receive focal lengths for at least one of said subarrays.

14. The apparatus of claim 1 further comprising a second filter for further spectral modification of said outputs from said first filter.

15. The apparatus in claim 14 further comprising a look-up table with settings for said second filter for at least some of said subarrays.

16. The apparatus of claim 15 further comprising a calculating unit for determining at least some settings for said second filter for at least some of said subarrays.

17. The apparatus of claim 14 wherein said second filter is selected from the group consisting of a 1-dimensional filter, a 2-dimensional filter and a 3-dimensional filter.

18. The apparatus of claim 14 wherein said first filter is varied for at least one of said receive focal lengths for at least one of said subarrays.

19. The apparatus of claim 1 wherein said first filter is a bandpass filter, wherein said subarrays have the same number of said adjacent transducer elements, and wherein overlap of said subarrays is equal to half of said number of said adjacent transducer elements in each of said subarrays.

20. The apparatus of claim 1 wherein said energy transmitted is in a range of frequencies selected from the group consisting of acoustic frequencies, optical frequencies, ultrasonic frequencies, sonic frequencies and radio frequencies.

21. The apparatus of claim 1 wherein interpolation in said first filter is varied for at least one of said subarrays.

22. The apparatus of claim 1 wherein said energy transmitted is in a narrowband of frequencies.

23. The apparatus of claim 1 wherein said energy transmitted is in a wideband of frequencies.

24. The apparatus of claim 1 wherein said energy is transmitted at a plurality of transmit focal lengths.

25. The apparatus of claim 1 wherein a number of receive directions $Q_{S2}$ in a second plane satisfies $$Q_{S2} \geq \frac{4M_2 d_2}{\lambda_{min}} \sin\left(\frac{\Theta_2}{2}\right),$$

where $M_2$ is a number of said adjacent transducer elements in a second dimension of each of said subarrays and said array, $d_2$ is a spacing between each of said adjacent transducer elements in said second dimension, $\Theta_2$ is a second sector angle in said second plane, and wherein an upsampling ratio $L_2$ in said second plane during interpolation in said first filter satisfies $$L_2 \geq \frac{\frac{4N_2 d_2}{\lambda_{min}} \sin\left(\frac{\Theta_2}{2}\right)}{Q_{S2}}$$

where $N_2$ is a total number of said transducer elements in said array in said second dimension.

26. A method of image reconstruction comprising:
 a) transmitting energy in a plurality of transmit directions with at least one transmit focal length with a subarray having adjacent transducer elements in an array of transducers, receiving responses to said energy and outputting receive signals with said subarray;
 b) spectrally modifying and interpolating between scan lines for a plurality of receive directions, $Q_S$, and receive focal lengths from said subarray with a first subarray-dependent filter;
 c) combining output from said first filter using a means to produce an intermediate result; and
 d) repeating steps a)-c) for a plurality of subarrays that define said array to produce a reconstructed image;
wherein a number of receive directions $Q_{S1}$ in a first plane satisfies $$Q_{S1} \geq \frac{4M_1 d_1}{\lambda_{min}} \sin\left(\frac{\Theta_1}{2}\right),$$

where $M_1$ is a number of said adjacent transducer elements in a first dimension of each of said subarrays and said array, $d_1$ is a spacing between each of said adjacent transducer elements in said first dimension, $\lambda_{min}$ is minimum wavelength in said transmitted energy, $\Theta_1$ is a first sector angle in said first plane, and wherein an upsampling ratio $L_1$ in said first plane in said interpolating satisfies $$L_1 \geq \frac{\frac{4N_1 d_1}{\lambda_{min}} \sin\left(\frac{\Theta_1}{2}\right)}{Q_{S1}}$$

where $N_1$ is a total number of said transducer elements in said array in said first dimension.

27. The method of claim 26 further comprising upsampling by inserting null scan lines for additional directions between said receive directions for said scan lines from said subarray, wherein said null scan lines are comprised of a set of zeros corresponding to each of said receive focal lengths.

28. The method of claim 26 wherein said transmitting of said energy and said receiving said response to said energy are performed by a first subarray.

29. The method of claim 26 wherein said transmitting of said energy is performed by a first subarray and said receiving said responses to said energy is performed by a second subarray.

30. The method of claim 26 wherein each of said subarrays has an equal number of adjacent transducer elements.

31. The method of claim 26 wherein each of said subarrays overlaps adjacent subarrays thereby having transducer elements in common with said adjacent subarrays.

32. The method of claim 31 wherein said overlap of said subarrays is a fixed number of said adjacent transducer elements in each of said subarrays.

33. The method of claim 26 further comprising looking up settings for said first filter in a look-up table for at least some of said subarrays.

34. The method of claim 33 further comprising calculating at least some settings for said first filter for at least some of said subarrays with a calculating means.

35. The method of claim 26 further comprising varying said first filter for at least one of said receive focal lengths for at least one of said subarrays.

36. The method of claim 26 further comprising spectrally modifying said outputs from said first filter with a second filter.

37. The method of claim 36 further comprising looking up settings for said second filter in a look-up table.

38. The method of claim 37 further comprising calculating at least some settings for said second filter for at least some of said subarrays with a calculating means.

39. The method of claim 38 further comprising varying said second filter for at least one of said receive focal lengths for at least one of said subarrays.

40. The method of claim 26 wherein said energy is in a range of frequencies selected from the group consisting of acoustic frequencies, optical frequencies, ultrasonic frequencies, sonic frequencies and radio frequencies.

41. The method of claim 26 wherein said transmitting said energy is in a narrowband of frequencies.

42. The method of claim 26 wherein said transmitting said energy is in a broadband of frequencies.

43. The method of claim 26 wherein a number of receive directions $Q_{S2}$ in a second plane satisfies $$Q_{S2} \geq \frac{4M_2 d_2}{\lambda_{min}} \sin\left(\frac{\Theta_2}{2}\right),$$

where $M_2$ is a number of said adjacent transducer elements in a second dimension of each of said subarrays and said array, $d_2$ is a spacing between each of said adjacent transducer elements in said second dimension, $\Theta_2$ is a second sector angle in said second plane, and wherein an upsampling ratio $L_2$ in said second plane in said interpolating satisfies $$L_2 \geq \frac{\frac{4N_2 d_2}{\lambda_{min}} \sin\left(\frac{\Theta_2}{2}\right)}{Q_{S2}},$$

where $N_2$ is a total number of said transducer elements in said array in said second dimension.

44. The method of claim 26 further comprising varying said interpolating in said first filter for at least one of said subarrays.

45. The method of claim 26 further comprising repeating said steps a)-c) for at least some of said subarrays and averaging said intermediate result corresponding to each repetition prior to step d) thereby improving signal-to-noise ratio.

46. The method of claim 26 further comprising repeating said step a) for at least some of said subarrays and averaging said receive signals corresponding to each repetition prior to step b) thereby improving signal-to-noise ratio.

47. The method of claim 26 further comprising transmitting said energy at a plurality of transmit focal lengths.

* * * * *

UNITED STATES PATENT AND TRADEMARK OFFICE
CERTIFICATE OF CORRECTION

| | | |
|---|---|---|
| PATENT NO. | : 7,972,271 B2 | Page 1 of 1 |
| APPLICATION NO. | : 11/709347 | |
| DATED | : July 5, 2011 | |
| INVENTOR(S) | : Jeremy A. Johnson | |

It is certified that error appears in the above-identified patent and that said Letters Patent is hereby corrected as shown below:

The following text should be inserted at col. 1, line 12:

--Statement of Government Sponsored Support
This invention was made with Government support under contract N00014-02-1-0007 awarded by the Department of the Navy ONR. The Government has certain rights in this invention.--

Signed and Sealed this
Twenty-eighth Day of February, 2012

David J. Kappos
*Director of the United States Patent and Trademark Office*